US005302716A

United States Patent [19]

Berger et al.

[11] Patent Number: 5,302,716

[45] Date of Patent: Apr. 12, 1994

[54] FUSED BENZAZEPINES

[75] Inventors: Joel G. Berger, Cedar Grove; Wei K. Chang, Livingston; Elijah H. Gold, West Orange; John W. Clader, Cranford, all of N.J.

[73] Assignee: Schering Corporation, Kenilworth, N.J.

[21] Appl. No.: 609,949

[22] Filed: Nov. 6, 1990

Related U.S. Application Data

[60] Division of Ser. No. 223,739, Jul. 18, 1988, Pat. No. 4,973,586, which is a continuation-in-part of Ser. No. 71,460, Jul. 9, 1987, abandoned, which is a continuation-in-part of Ser. No. 3,874, Jan. 16, 1987, abandoned, which is a continuation-in-part of Ser. No. 820,471, Jan. 16, 1986, abandoned.

[51] Int. Cl.[5] .................... C07D 223/14; C07D 223/32

[52] U.S. Cl. .................................................... 540/519

[58] Field of Search ......................... 514/213; 540/519

[56] References Cited

U.S. PATENT DOCUMENTS

| | | | |
|---|---|---|---|
| 3,393,192 | 7/1968 | Walter et al. | 260/239 |
| 3,609,138 | 9/1971 | Mull et al. | 260/239 |
| 3,939,165 | 2/1976 | Schwan | 260/230 R |
| 4,011,319 | 3/1977 | Kaiser, et al. | 260/239 |
| 4,284,555 | 8/1981 | Gold et al. | 260/239 BB |
| 4,315,926 | 2/1982 | Gschwend | 260/239 D |
| 4,356,176 | 10/1982 | Gschwend | 514/217 |
| 4,415,495 | 11/1983 | Satzinger et al. | 260/239 D |
| 4,477,378 | 10/1984 | Gold et al. | 260/239 BB |
| 4,973,586 | 11/1990 | Berger et al. | 514/217 |

FOREIGN PATENT DOCUMENTS

| | | |
|---|---|---|
| 2137626 | 12/1972 | France . |
| 1118688 | 7/1968 | United Kingdom . |
| 1221324 | 2/1971 | United Kingdom . |

OTHER PUBLICATIONS

Derwent Abstract NE 68 02257, Published Aug. 19, 1968.

*Primary Examiner*—David B. Springer
*Attorney, Agent, or Firm*—Edward H. Mazer; Warrick E. Lee, Jr.; James R. Nelson

[57] ABSTRACT

Disclosed are fused benzazepine compounds, pharmaceutical compositions including such compounds, methods of using such compounds, for example, in the treatment of psychoses and/or depression, and intermediates useful in the preparation of such compounds.

9 Claims, No Drawings

FUSED BENZAZEPINES

This is a divisional of U.S. application Ser. No. 07/223,739 filed Jul. 18, 1988, U.S. Pat. No. 4,973,586 which in turn is a continuation-in-part of U.S. application Ser. No. 071,460, abandoned, filed Jul. 9, 1987, abandoned which in turn is a continuation-in-part of U.S. application Ser. No. 003,874, filed Jan. 16, 1987, abandoned, which in turn is a continuation-in-part of U.S. application Ser. No. 820,471, filed Jan. 16, 1986, abandoned.

BACKGROUND OF THE INVENTION

This invention relates to fused derivatives of compounds having a fused ring nucleus which includes a 2,3,4,5-tetrahydro-1H-3-benzazepine system, to methods for their preparation, to intermediates useful in their preparation, and to pharmaceutical compositions containing them. The compounds have valuable pharmaceutical properties in the treatment of psychoses, depression, pain and hypertension.

Substituted 1-phenyl-2,3,4,5-tetrahydro-1H-3-benzazepines have been described in the art. For example, see U.S. Pat. Nos. 3,393,192, 3,609,138, 4,011,319, 4,284,555 and 4,477,378 as well as British Patent 1,118,688. The activities discussed for the compounds disclosed in these patents include antibacterial effects, central nervous system effects and hypotensive effects.

SUMMARY OF THE INVENTION

This invention relates to compounds according to the structural formula I, including all isomers and pharmaceutically acceptable salts thereof,

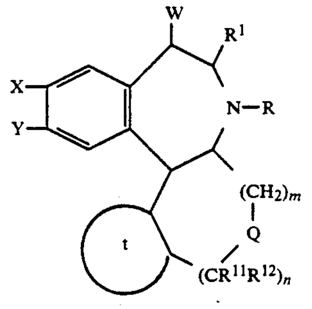

I wherein:

R is hydrogen, alkyl, $-CH_2CH{=}CH_2$ or

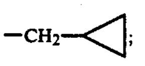

$R^1$, $R^{11}$ and $R^{12}$ may be the same or different and each is hydrogen or alkyl;

Q is methylene, —O— or —S—;

m and n are independently variable and may each have a value of 0, 1 or 2, with the provisos that the sum of m and n is not greater than 3, and that m may not equal zero when Q is —O— or —S—;

X is hydrogen, halo, alkyl, alkylthio, alkylsulfinyl, alkylsulfonyl, hydroxy, alkoxy or trifluoromethyl;

Y is hydrogen, hydroxy, alkoxy, 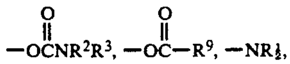 $-NR^1_2$,

-continued

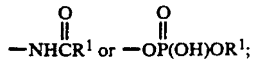

W is hydrogen, hydroxy or alkoxy;

ring

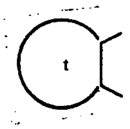

represents a fused thiophene or fused benzene ring, said fused benzene ring optionally being substituted with a substituent Z as defined below;

$R^2$ and $R^3$ are independently hydrogen (provided that both are not hydrogen), alkyl, aralkyl, cycloalkyl, aryl, hydroxyalkyl, or alkoxyalkyl;

in addition, when one of $R^2$ and $R^3$ is as defined above, the other may be $-R^4NR^5R^6$ {wherein $R^4$ is alkanediyl, $R^5$ is hydrogen or alkyl and $R^6$ is alkyl, or $R^5$ and $R^6$ together with the nitrogen atom form a 1-azetidinyl, 1-pyrrolidinyl, 1-piperidinyl, 1-(4-alkylpiperazinyl), 4-morpholinyl or 1-(hexahydroazepinyl) group};

in further addition, $R^2$ and $R^3$ together with the nitrogen atom may form a 1-azetidinyl, 1-pyrrolidinyl, 1-piperidinyl, 4-morpholinyl, 1-(4-alkylpiperazinyl), 1-(4-alkoxyalkylpiperazinyl), 1-(4-hydroxyalkylpiperazinyl), 1-(3-hydroxyazetidinyl), 1-(3-alkoxyazetidinyl), 1-(3-hydroxypyrrolidinyl), 1-(3-alkoxypyrrolidinyl), 1-(3- or 4-hydroxypiperidinyl), 1-(3- or 4-alkoxypiperidinyl), 1-(4-oxopiperidinyl) or 1-(3-oxopyrrolidinyl) ring;

in still further addition, when $R^2$ is hydrogen, $R^3$ may be $-CHR^7CO_2R^8$, wherein $R^7$ and $R^8$ are independently hydrogen, alkyl or aralkyl;

$R^9$ is alkyl, aralkyl, aryl, alkoxyalkyl, aryloxyalkyl, aralkoxyalkyl, cycloalkylalkyl, alkoxycarbonylalkyl, cycloalkyl, 1-adamantyl, cycloalkoxyalkyl, alkoxy, aralkoxy, cycloalkoxy, aryloxy or $-CHR^7NHR^8$ {wherein $R^7$ and $R^8$ are as defined above}; and Z is X as defined above, amino, alkylamino or

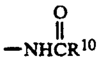

{wherein $R^{10}$ is hydrogen, alkyl or aryl}.

The present invention also includes intermediates useful in the preparation of the compounds of formula I, i.e., intermediates of formula II, XI or XIV

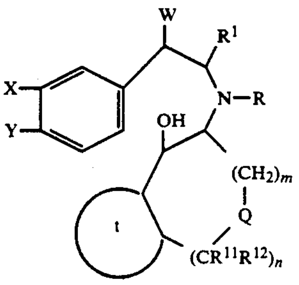

II

-continued

XI

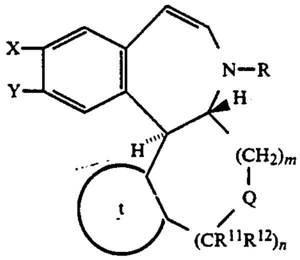

XIV

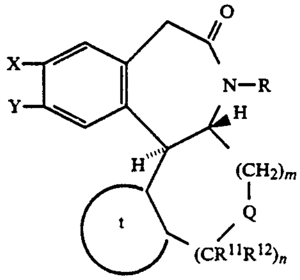

including all isomers and salts thereof, wherein R, $R^1$, $R^{11}$, $R^{12}$, W, X, Y, Z, Q, m, n and ring

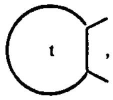

, are as defined above.

A preferred subgenus of compounds of formula I is represented by structural formula Ia below:

Ia

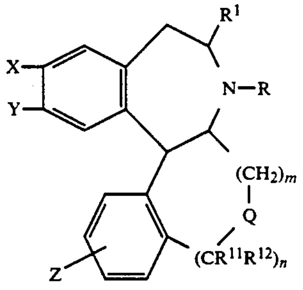

wherein R, $R^1$, $R^{11}$, $R^{12}$, X, Y, Z, Q, m and n are as defined above.

Y is preferably selected from

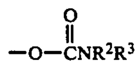

(wherein $R^2$ and $R^3$ are both alkyl or one of $R^2$ and $R^3$ is hydrogen and the other is alkyl), $—NHR^1$ (wherein $R^1$ is hydrogen or methyl),

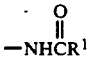

(wherein $R^1$ is hydrogen or methyl),

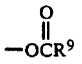

(wherein $R^9$ is as defined above) or hydroxy, and more preferably, Y is amino or hydroxy. W is preferably H. X is preferably hydrogen, alkyl, halogen or alkoxy; while Z is preferably hydrogen, halogen, alkyl, hydroxy or alkoxy. R is preferably methyl and $R^1$ is preferably hydrogen or methyl, more preferably hydrogen. Ring

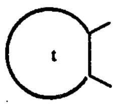

preferably represents a fused benzene ring optionally substituted with halo, alkyl, or $—OR^1$.

A particularly preferred subgenus of compounds is that of formula Ia above wherein R is methyl; $R^1$ is hydrogen; Q is methylene; the sum of m and n equals 1; X is hydrogen, methyl, methoxy, chloro or bromo; Y is hydroxy, amino,

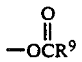

(wherein $R^9$ is defined as above),

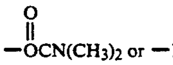 or $—NHCH_3$;

and Z is hydrogen, halo, alkyl or $—OR^1$ (wherein $R^1$ is hydrogen or alkyl); or a pharmaceutically acceptable salt of such a compound.

Examples of preferred compound are:

(1) 6,7,7a,8,9,13b-hexahydro-2-hydroxy-3-methoxy-7-methyl-5H-benzo[d]naphtho[2,1-b]azepine;

(2) 6,7,7a,8,9,13b-hexahydro-2-hydroxy-7-methyl-5H-benzo[d]naphtho[2,1-b]azepine;

(3) 6,7,7a,8,9,13b-hexahydro-3-chloro-2-hydroxy-7-methyl-5H-benzo[d]naphtho[2,1-b]azepine;

(4) 6,7,7a,8,9,13b-hexahydro-2-hydroxy-3,7-dimethyl-5H-benzo[d]naphtho[2,1-b]azepine;

(5) 6,7,7a,8,9,13b-hexahydro-2-amino-7-methyl-5H-benzo[d]naphtho[2,1-b]azepine;

(6) 6,7,7a,8,9,13b-hexahydro-2-amino-3-chloro-7-methyl-5H-benzo[d]naphtho[2,1-b]azepine;

(7) 6,7,7a,8,9,13b-hexahydro-2-amino-3,7-dimethyl-5H-benzo[d]naphtho[2,1-b]azepine;

(8) 6,6a,7,8,9,13b-hexahydro-12-methoxy-7-methyl-[1]benzopyrano[4,3-a][3]benzazepine;

(9) 6,6a,7,8,9,13b-hexahydro-7-methyl[1]benzopyrano[4,3-a][3]benzazepin-12-ol;

(10) 6,6a,7,8,9,13b-hexahydro-3-hydroxy-2-methoxy-7-methyl-5H-benzo[d]naphtho[2,1-b]azepine;

(11) 2-hydroxy-3-methoxy-7-methyl-5,6,7,7a,8,9,10,14b-octahydro-benzo[d]benzo[3,4]cyclohepta[1,2-b]azepine;

(12) 3-hydroxy-2-methoxy-7-methyl-5,6,7,7a,8,9,10,14b-octahydro-benzo[d]benzo[3,4]cyclohepta[1,2-b]azepine;

(13) 5,6,7,7a,8,12b-hexahydro-2-hydroxy-3-chloro-7-methyl-benz[d]indeno[2,1-b]azepine;

(14) 5,6,7,7a,8,12b-hexahydro-2-hydroxy-3-methoxy-7-methyl-benz[d]indeno[2,1-b]azepine;
(15) 5,6,7,7a,8,12b-hexahydro-2-amino-3-chloro-7-methyl-benz[d]indeno[2,1-b]azepine;
(16) 5,6,7,7a,8,12b-hexahydro-2-hydroxy-7-methyl-benz[d]indeno[2,1-b]azepine;
(17) 5,6,7,7a,8,12b-hexahydro-3,7-dimethyl-2-hydroxy-benz[d]indeno[2,1-b]azepine;
(18) 5,6,7,7a,8,12b-hexahydro-3-chloro-7-cyclopropyl-methyl-2-hydroxy-benz[d]indeno[2,1-b]azepine;
(19) 5,6,7,7a,8,12b-hexahydro-7-allyl-3-chloro-2-hydroxy-benz[d]indeno[2,1-b]azepine;
(20) 5,6,7,7a,8,12b-hexahydro-3-chloro-2-hydroxy-7,8,8-trimethyl-benz[d]indeno[2,1-b]azepine;
(21) 5,6,7,7a,8,11b-hexahydro-3-chloro-7-methyl-thieno[2',3':4,5]cyclopenta[1,2-a]-[3]benzazepine-2-ol;
(22) 5,6,7,7a,8,12b-hexahydro-2-hydroxy-3-chloro-benz[d]indeno[2,1-b]azepine;
(23) 6,7,7a,8,9,13b-hexahydro-3-chloro-2-hydroxy-5H-benzo[d]naphtho[2,1-b]azepine;
(24) 6,7,7a,8,9,13b-hexahydro-2-amino-3-trifluoromethyl-7-methyl-5H-benzo[d]naphtho[2,1-b]azepine; or a pharmaceutically acceptable salt and/or trans isomer of such compounds.

When utilized herein and in the appended claims, the following terms, unless otherwise specified, have the following scope:

halo—represents fluoro, chloro, bromo or iodo;

alkyl (including, for example, the alkyl portions of alkylthio, alkoxy, aralkyl, alkoxyalkoxy, etc.)—represents straight or branched carbon chains having 1 to 6 carbon atoms;

cycloalkyl groups (including the cycloalkyl portion in cycloalkoxy groups)—represents saturated carbocyclic rings having 3 to 7 carbon atoms;

alkanediyl—represents a divalent, straight or branched hydrocarbon chain having from 1 to 6 carbon atoms, the two available bonds being from the same or different carbon atoms thereof, e.g., methylene, ethylene, ethylidene, $$-CH_2CH_2CH_2-,\ -CH_2\overset{|}{C}HCH_3,\ -\overset{|}{C}HCH_2CH_3,\ \text{etc.};$$

and aryl (including, for example, the aryl moiety in aralkyl or aralkoxy groups)—represents unsubstituted phenyl and phenyl mono substituted by alkyl, hydroxy, alkoxy, halo or trifluoromethyl.

The compounds of formula I possess analgesic, antiaggressive and general tranquilizing properties. The invention therefore includes pharmaceutical compositions comprising a compound of formula I in combination with a pharmaceutically acceptable carrier and methods for treating mental disorders including psychoses, schizophrenia or depression in a mammal, or for the control of pain or anxiety in a mammal by administering an effective amount of a compound of formula I to the affected mammals. The compounds of formula I provide a long duration of activity.

Certain compounds of formula I wherein X and Y are hydroxy and R is hydrogen are also active as renal vasodilators. These compounds can thus be used in pharmaceutical compositions in combination with a pharmaceutically acceptable carrier and in methods for controlling hypertension by administering to a mammal a renal vasodilating effective amount of such a compound.

DETAILED DESCRIPTION OF THE INVENTION

Compounds according to formula II may exist as diastereomers. Specifically, the hydrogen bonded to the carbon bearing the hydroxyl group and the hydrogen bonded to the adjacent saturated carbon atom may be cis or trans to each other. Upon condensation, the fused ring systems of formula I may be joined cis (formula III) or trans (formula IV) and are, therefore, also diastereomers:

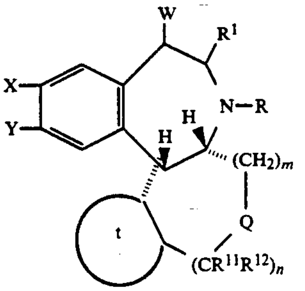

III

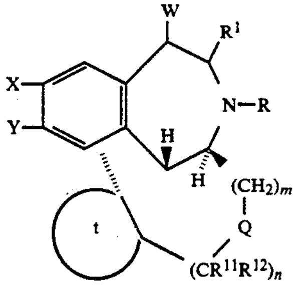

IV

The trans form (formula IV) of the compounds of formula I i.e. the compounds of formula IV is a preferred embodiment. It is noted that, when $R^1$ and/or W is other than hydrogen and when $R^{11}$ and $R^{12}$ are different, at least one other asymetric center exists in the compounds of the invention. All such isomeric forms and mixtures thereof are within the scope of the present invention. Unless otherwise indicated, the methods of preparation disclosed herein result in product distributions which include all possible structural isomers, although it is understood that physiological response may vary according to stereochemical structure. The isomers may be separated by conventional means such as fractional crystallization or HPLC.

Ring

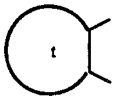

may represent a fused thiophene ring. The sulfur atom in such fused thiophene ring may be in any of the non-fused positions of said ring.

Compounds of formulas I, II, XI and XIV can exist in unsolvated as well as solvated forms, including hydrated forms. In general, the solvated forms, with pharmaceutically acceptable solvents such as water, ethanol and the like are equivalent to the unsolvated forms for purposes of this invention.

The compounds of formulas I, II, XI and XIV may form pharmaceutically acceptable salts with organic and inorganic acids. Examples of suitable acids for salt formation are hydrochloric, sulfuric, phosphoric, acetic, citric, malonic, salicylic, malic, fumaric, succinic, ascorbic, maleic, methanesulfonic and other mineral and carboxylic acids well known to those in the art. The salts are prepared by contacting the free base form with a sufficient amount of the desired acid to produce a salt in the conventional manner. The free base forms may be regenerated by treating the salt with a suitable dilute aqueous base solution such as dilute aqueous sodium hydroxide, potassium carbonate, ammonia and sodium bicarbonate. The free base forms differ from their respective salt forms somewhat in certain physical properties, such as solubility in polar solvents, but the salts are otherwise equivalent to their respective free base forms for purposes of the invention.

The compounds of formula I above may be prepared by the methods A–C described below:

(A) An intramolecular condensation of a compound of the formula

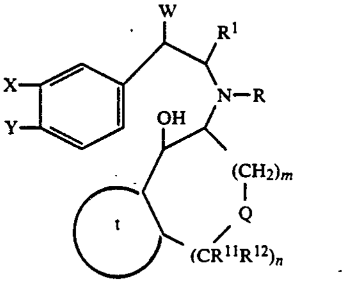

II in the presence of a dehydration catalyst will result in a compound of formula I. Effective dehydration catalysts include sulfuric acid, methanesulfonic acid, trifluoromethanesulfonic acid, phosphoric acid and anhydrous hydrofluoric acid.

The intramolecular condensation described above may be performed at various temperatures and pressures, e.g., between 0° C. and 100° C. and at reduced, atmospheric/or elevated pressure. An inert solvent may be employed or the reaction may be run in the absence of solvent. The time required for obtaining the desired product varies somewhat with the temperature, pressure and batch size but the reaction is generally complete within 24 hrs.

i. Compounds of formula II may be obtained by reacting an amine of formula V with a compound of formula VI

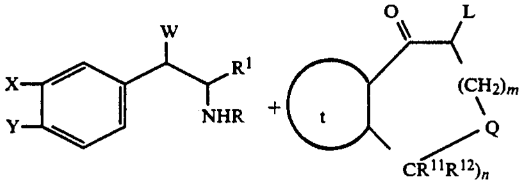

V VI to produce a compound of formula VII

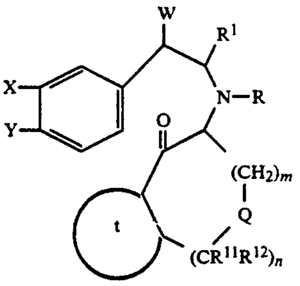

VII followed by reduction of the carbonyl group in the product of formula VII to hydroxy. The symbol L represents a readily displaceable moiety commonly known as a "leaving group". Suitable leaving groups used by those skilled in the art include but are not limited to the halides, e.g., chlorine, bromine or iodine, and $OSO_2R'$ wherein R' may be hydrogen, alkyl, perfluoroalkyl, arylalkyl, or aryl (for example para-toluenesulfonyl). Preferred reducing agents for the reduction step include $NaBH_4$, $LiAlH_4$, $BH_3$, and $NaAlH_2(OCH_2CH_2OCH_3)_2$. Catalytic reductions using catalysts such as palladium on carbon or Raney nickel and hydrogen gas at 1 to 10 atmospheres pressure are also effective.

ii. Compounds of formula II may also be obtained by reacting an amine of formula VIII with a compound of formula IX under the conditions described in the preceding paragraph but without the reduction step:

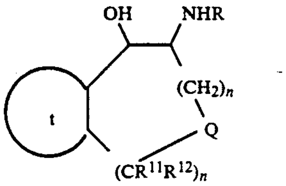

VIII

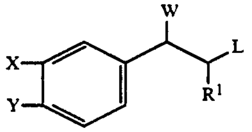

IX iii. Compounds of formula II can be prepared by reacting an aldehyde ($R^1$=H) or ketone ($R^1$=alkyl) of formula X with an amino alcohol of formula VIII in the presence of an appropriate reducing agent such as sodium cyanoborohydride at pH 4–7.

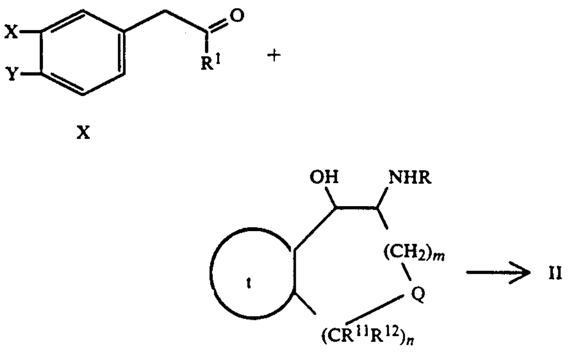

X + VIII → II iv. Compounds of formula II may also be prepared by reaction of compounds of formula VIII with aldehydes or ketones of formula X with prior removal of water of condensation followed by reduction of the resulting intermediate condensation product with reducing agents such as $NaBH_4$ or $NaCNBH_3$, or by catalytic reduction using catalysts such as palladium on carbon or Raney nickel under a hydrogen atmosphere at 1-10 atmospheres pressure.

(B) Compounds of formula I also may be prepared by reacting a compound of the formula

XI

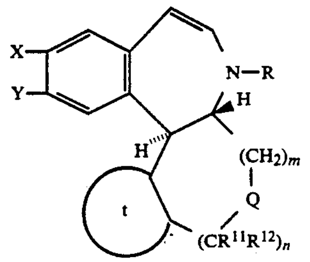

with a suitable reducing agent to produce the compound of formula I. Preferred reducing agents comprise hydrogen and a reducing catalyst, preferably $PtO_2$ or platinum on carbon, or sodium cyanoborohydride at pH 4-7 in a suitable solvent, e.g. ethanol.

The compound of formula XI may be prepared, for example, by reacting a compound of formula XII with a 1-halo-2,2-dialkoxyethane in the presence of a suitable solvent such as dimethylformamide (DMF) and a catalyst such as an alkali metal iodide, preferably potassium iodide, to produce a compound of formula XIII, where R' is $C_1$-$C_3$ alkyl.

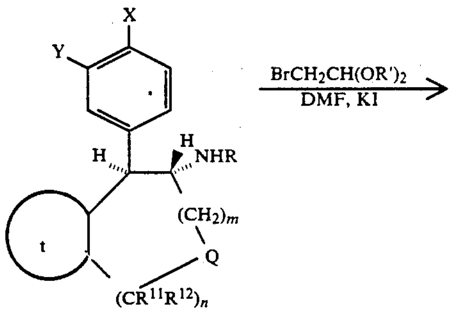

XII

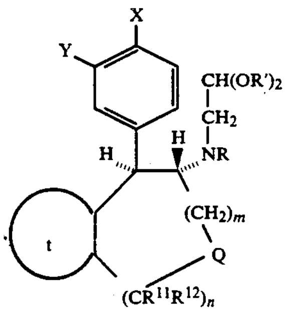

XIII

The compound of formula XIII may be reacted with a strong acid such as trifluoromethane sulfonic acid, methane sulfonic acid, or sulfuric acid at a temperature ranging between about 0°-25° C., to produce the compound of formula XI and in addition compounds of formula I wherein W is OH or OR'.

C. Compounds of formula I also may be prepared by reacting a compound of formula XIV

XIV

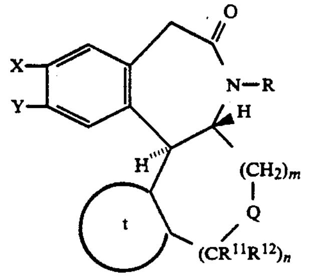

with a reducing agent such as $LiAlH_4$ or $BH_3$, preferably $BH_3$, at a temperature ranging between about 0° C. and about 70° C. to produce the compound of formula I.

One method for preparing the compounds of formula XIV is set forth below. This method is particularly applicable where Y is OH or alkoxy. Where Y is one of the other substituents defined, additional process steps known in the art may be used to convert the OH and alkoxy groups to other Y substituents.

The compounds of formula XIV may be prepared by reacting a compound of formula XV with an appropriate Grignard reagent XVa

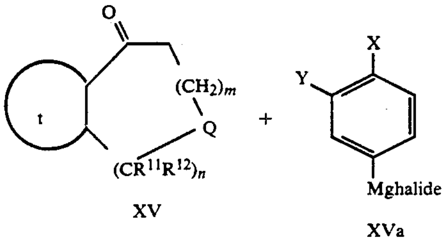

XV XVa to produce a compound of the formula XVI

XVI

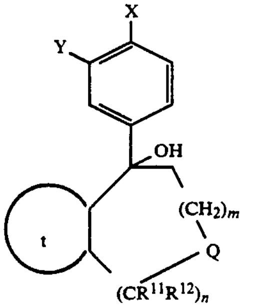

which may be dehydrated to a compound of formula XVII using acidic catalysts such as toluene sulfonic acid or phosphorus oxychloride/pyridine at a temperature ranging between about 20° C. and about 120° C. with continuous removal of water.

XVII

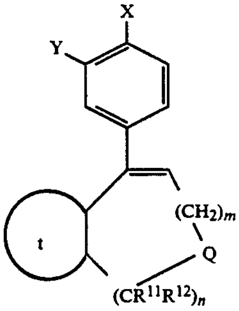

The compound of formula XVII may be oxidized to produce a compound of formula XVIII below using m-chloroperbenzoic acid at a temperature ranging between about 0° C. and about 20° C., followed by contact with an alkali metal hydroxide such as sodium hydroxide, which is followed by contact with a strong mineral acid.

XVIII

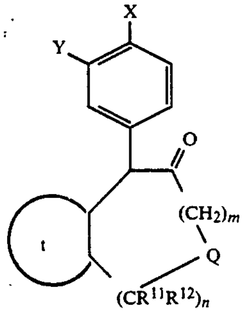

The compounds of formula XVIII may in turn be reacted with an alkyl amine with continuous removal of water to produce a compound of formula XIX

XIX

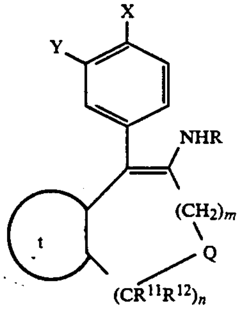

which then may be reduced in the presence of a catalyst such as zinc dust and acetic acid or sodium cyanoborohydride in the presence of acetic acid to produce a compound of formula XX

XX

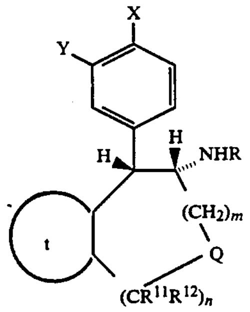

which may then be treated with a strong base in dimethylsulfoxide (DMSO) or a mixed solvent comprising DMSO plus a polar aprotic solvent, e.g., dimethylformamide (DMF), to produce a compound of formula XXI. Strong bases utilized are preferably potassium tert butoxide or sodium hydride.

XXI

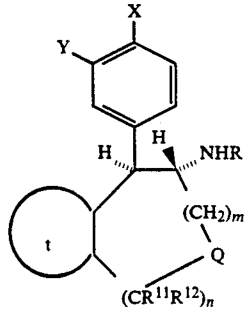

Alternatively, the compound of formula XVII may be reacted with $BH_3$-methyl sulfide complex in a halo carbon solvent (e.g. $CH_2Cl_2$) at temperature of 20°-65°, and the resulting reaction mixture treated with hydroxylamine-O-sulfonic acid at temperatures of 80°-120° C. in a mixed solvent system such as diglyme/$CH_2Cl_2$ to furnish compounds of formula XXI with R=H.

The compound of formula XXI may be contacted with a haloacetyl halide to produce a compound of formula XXII

XXII

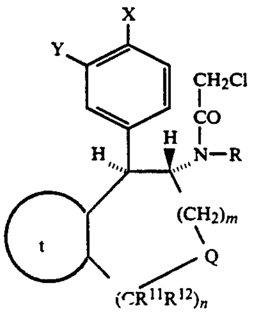

which may be exposed to ultraviolet light to produce the compound of formula XIV

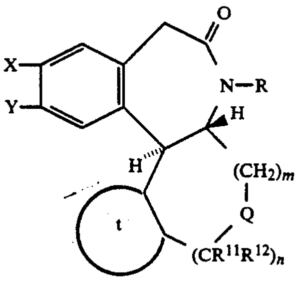

XIV which may then be reduced to the compound of formula I.

The above processes A–C are equally applicable to trans and cis forms of the claimed compounds although in some instances only the trans forms are shown.

In the above processes A–C, it is sometimes desirable and/or necessary to protect certain R, $R^1$, $R^{11}$, $R^{12}$, W, X, Y and Z groups during the reactions. Conventional protecting groups are operable. For example, the groups listed in column 1 of the following table may be protected as indicated in column 2 of the table:

| 1. Group to be Protected | 2. Protected Group |
|---|---|
| —COOH | —COOalkyl, —COObenzyl, —COOphenyl |
| >NH | >N—$CO_2$alkyl, >N—$CO_2$benzyl, >N—$CO_2CH_2CCl_3$ |
| >CO | 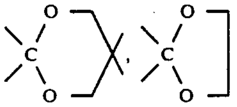 |
| —OH | 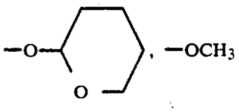, —$OCH_3$ |
| —$NH_2$ | 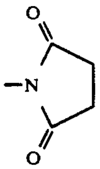 |

Of course, other protecting groups well known in the art may be used. After the reaction or reactions, the protecting groups may be removed by standard procedures.

Also, R, $R^1$, $R^{11}$, $R^{12}$, W, X, Y and Z groups in formula I may be varied by appropriate selection of starting materials from which the compounds are synthesized or by reacting a compound of formula I with a suitable reagent to effect the desired conversion of the substituent to another R, $R^1$, $R^{11}$, $R^{12}$, W, X, Y and Z group. The latter procedure is particularly applicable for changing the substituents X. For example, a chlorine substituent may be added in place of hydrogen by reaction with a chlorinating agent such as sulfuryl chloride in a non-reactive solvent. A hydroxymethyl substituent in the X position may be added in place of hydrogen by reaction with formaldehyde in a suitable solvent system, e.g., in a mixed solvent system consisting of dimethyoxyethane and aqueous potassium hydroxide, preferably at an elevated temperature. Such a hydroxymethyl substituent may be reduced to an X methyl group by reaction with a catalyst such as palladium hydroxide in a hydrogen atmosphere under pressure. Methoxy substituents may be converted to hydroxy, e.g., by refluxing in a mixture of sodium hydride, DMF and ethanethiol, or by reaction with concentrated hydrobromic acid. Other substitutions may be accomplished using standard techniques.

The compounds of formula I display pharmacological activity in test procedures designed to indicate antipsychotic and anti-depressive activity.

CONDITIONED AVOIDANCE SUPPRESSION IN RATS

Clinically active antipsychotic drugs are known to depress discrete trial avoidance behavior at doses that do not retard escape response (Ann. N.Y. Acad. Sci. 66, 740 (1957)). A series of experiments was carried out to assess the ability of the compounds of this invention to suppress the conditioned avoidance response (CAR) in rats.

Materials and Methods

Rats were required to jump onto a platform located 6.75 inches (17.15 cm) above the grid floor of an experimental chamber in response to a 5-second tone to avoid a 10-second foot shock (0.6 ma). Each experimental session consisted of 20 such trials presented at 30-second intervals. A correct CAR is scored whenever the rat jumps onto the platform during the tone (prior to foot shock). An escape response is scored when the rat jumps onto the platform during a shock. A response failure is defined as the lack of an escape response during the 10-second shock period.

Groups of 6–8 rats were trained in two consecutive days (total of 40 trials). Rats that reached criterion on day 2 (correct CARs on 16 or more of the 20 trials) were treated with either a test drug or vehicle on day 3. Suppression of CAR was analyzed statistically using Student's t-test comparing the performance of rats on day 2 with their performance following drug on day 3. The minimal effective dose (MED) for each drug is defined as the lowest dose tested that significantly ($p \leq 0.05$) reduced avoidance responding.

Results

The results in the above procedure with representative compounds of the invention are shown in column 8 of Table I below.

SQUIRREL MONKEY CONDITIONED AVOIDANCE RESPONSE (CAR) TEST

This test was designed to measure the effective duration of candidate compounds.

Male or female squirrel monkeys weighing 800–1200 g housed one per cage were utilized. Initially each monkey was taught to terminate a 3 mA electric shock delivered through the grid floor of the test cage and an overlapping tone by depressing a lever in the cage. The monkeys did not proceed to the second phase of testing unless they depressed the lever during the shock component of the trials at least 75% of the time during 60 daily trials on three consecutive days.

In the second phase of the testing, a ten second tone is turned on prior to the shock component. A lever press during the sounding of the tone terminates the tone and prevents the occurrence of the shock component and is denoted as an "avoidance". Compound testing does not begin until the monkey makes at least 85% correct avoidances for five consecutive days.

The compound testing was commenced after three consecutive days of re-testing. The monkey first was injected or orally dosed with the vehicle only and retested to show that the vehicle does not affect the response of the monkey. The monkey must achieve at least an 85% correct avoidance before drug testing commences. If this minimal avoidance level is achieved, the next day the monkey is orally dosed or injected with the subject compounds in the appropriate vehicle and the number of avoidances are recorded. An animal is defined as having been "affected" by any drug treatment if there is a 50% loss of avoidance behavior relative to the performance of the animal when only the vehicle was injected. The minimal effective dose (MED) is defined as that dose producing an effect in at least 50% of the animals.

A test was conducted to determine the effective duration of a compound of the present invention, 6,7,7a,8,9,13b-hexahydro-3-chloro-2-hydroxy-7-methyl-5H-benzo[d]naphtho[2,1-b]azepine, denoted as Compound A, compared to a known compound, (d)-7-chloro-8-hydroxy-3-methyl-1-phenyl-2,3,4,5-tetrahydro-1h-3-benzazepine maleate, denoted as Compound B (Sch 23390)

It was determined that the $ED_{50}$ (approximately 1.6 mg/kg po) of Compound A administered 60 minutes prior to the test was roughly equivalent to the $ED_{50}$ (2.4 mg/kg po) of compound B administered 30 minutes prior to test. The duration of each compound was determined by administering a 10 mg/kg po dose six hours prior to testing. The ability to significantly decrease the number of avoidances six hours after injection was used to indicate that the compound was still active at that time. The tests showed that Compound A caused a significant decrease in the number of avoidances ($p \leqq 0.05$) whereas Compound B was inactive at that time. These results are presented below in Table II where N is the number of monkeys tested.

TABLE II

| TREATMENT | DOSE (p.o.) (mg/kg) | N | MEAN (±SE) NUMBER OF AVOIDANCES AT 6 HOURS POST-TREATMENT |
|---|---|---|---|
| Vehicle | — | 7 | 59.1 + 0.9 |
| Compound A | 10 | 7 | 23.9 + 7.5 |
| Compound B | 10 | 3 | 59.7 + 0.3 |

COMPETITIVE INHIBITION ASSAY

Many compounds capable of effecting reproducible physiological changes in neural tissues are believed to operate by binding at one or more receptor sites. Compounds which interact strongly with these receptor sites in in vitro tests, using homogenates of the target organ or structure, are expected to exhibit similar properties when administered in vivo and are, therefore, candidates for continued study as potential therapeutic and/or diagnostic agents.

Binding of a compound to a receptor site, in vitro, is demonstrated by the specificity of binding and the saturability of the available sites. A methodology for characterization of D-1 and D-2 receptor binding and an interpretation of the data are described by Billard et al., *Life Sciences* 35, 1885 (1984) in which the binding of the benzazepine (R)-(+)-8-chloro-2,3,4,5-tetrahydro-3-methyl-5-phenyl-1H-3-benzazepin-7-ol hemimaleate (SCH 23390) to the dopamine D-1 receptor is characterized. A selectivity for D-1 receptor binding as compared to D-2 receptor binding is believed to confer the therapeutic advantage of avoiding troublesome and potentially irreversible neurological side effects associated with D-2 receptor occupancy.

Materials and Methods

Tritiated SCH 23390 and tritiated spiperone (a potent D-2 receptor ligand) were obtained as described in the Billard et al. reference supra and serially diluted in 0.05M Tris buffer, pH 7.4, as required. Compounds of this invention were synthesized as disclosed herein and diluted in 0.05M Tris buffer, pH 7.4, as required.

Tissue Preparation

Male Sprague-Dawley rats (200 to 250 g) from Charles River Breeding Laboratories, Mass. were used to obtain brain tissue. The rats were humanely sacrificed and their brains removed and placed on ice. Striatal tissue was excised, pooled, and homogenized (Brinkman Polytron, 10 sec) in 100 volumes (w/v) of ice cold 50 mM Tris buffer, pH 7.4 (at 25° C.). The homogenate was centrifuged at 20,000× g for 10 min. The resultant pellet was rehomogenized in Tris buffer and centrifuged again. The final pellet was resuspended in 50 mM Tris buffer pH 7.4 containing 120 mM NaCl, 5 mM KCl, 2 mM $CaCl_2$, and 1 mM $MgCl_2$.

Assay

Polypropylene incubation tubes received 100 μl of the individual test compounds at various concentrations dissolved or suspended in 0.05M Tris, pH 7.4 containing 4 mg/ml methylcellulose, 100 μl of a solution of $^3$H-SCH 23390 in Tris buffer (final reaction mixture concentration =0.3 nM) or 100 μl of a solution of $^3$H-spiperone in Tris buffer (final concentration =0.2 nM) and 800 μl of tissue suspension (ca. 3 mg/assay). Tubes were incubated at 37° C. for 15 minutes and rapidly vacuum filtered through Whatman GF/B filters and rinsed 4 times with 4 ml of ice cold 50 mM Tris buffer, pH 7.4. The filters were transferred to scintillation vials, equilibated with 10 ml of scintillant (Scintosol, Isolab, Inc.) for 16 hours at 25° C. and the radioactivity determined in a liquid scintillation counter. $K_i$ values were determined as described by Billard et al. using the relationship $K_i = IC_{50}/(1+([L]/K_D))$ wherein $IC_{50}$ = concentration of test drug necessary to displace 50% of specifically bound $^3$H-Sch 23390, [L]=concentration of radioligand used in the assay, and $K_D$=dissociation constant.

Results

The inhibition constants ($K_i$) determined from the assays for a series of compounds of the invention are as shown in columns 6 and 7 of Table I below.

TABLE I

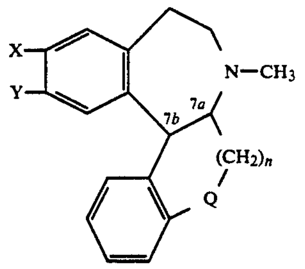

| Col. 1 Q | Col. 2 n | Col. 3 stereo-chemistry of 7a and 7b H's | Col. 4 X | Col. 5 Y | Col. 6 Ki (nM) $^3$H-23390 | Col. 7 Ki (nM) $^3$H-Spip | Col. 8 CAR(MED) |
|---|---|---|---|---|---|---|---|
| $CH_2$ | 1 | cis | $CH_3O$ | OH | 6450 | >100,000 | |
| $CH_2$ | 1 | cis | HO | $CH_3O$ | 44,800 | >100,000 | |
| $CH_2$ | 1 | trans | $CH_3O$ | OH | 23 | 2500 | 30 (po); 0.3-1 (sc) |
| $CH_2$ | 1 | trans | HO | $CH_3O$ | 2970 | >100,000 | |
| $CH_2$ | 1 | trans | Cl | OH | 5.5 | 11,500 | 30 (po); 0.3 (sc) |
| $CH_2$ | 1 | 7b(S):7a(R)(+) | Cl | OH | 1800 | >100,000 | >30 (po) |
| $CH_2$ | 1 | 7b(R):7a(S)(−) | Cl | OH | 12 | 14,300 | 30 (po) |
| $CH_2$ | 1 | cis | Cl | OH | 6200 | >100,000 | |
| $CH_2$ | 1 | trans | H | OH | 80 | 3500 | |
| $CH_2$ | 2 | trans | $CH_3O$ | OH | 292 | >100,000 | 10 (sc) |
| $CH_2$ | 2 | trans | HO | $CH_3O$ | 7730 | >100,000 | 10 (sc) |
| $CH_2$ | 1 | trans | $CH_3$ | OH | 119 | 7200 | |
| $CH_2$ | 1 | trans | Cl | $NH_2$ | 70 | 4175 | 3 (po) |
| O | 1 | trans | H | OH | 121 | — | |
| $CH_2$ | 0 | trans | Cl | OH | 10 | 2600 | |

The comparatively small $K_i$ values of these compounds in the competitive binding assay with SCH 23390 indicate that the compounds of formula I bind strongly to the D-1 receptor site. The relatively high $K_i$ values for the D-2 site, for which spiperone is highly selective, indicate that the compounds are not specifically bound to that receptor site.

Selective activity for D1 receptors is indicative of these compounds' potential use as D1 antagonists in treating disorders that may be lessened by D1 antagonists as discussed in Beaulieu, Canadian J. Neur. Sci. 14(3):402 (1987) and Waddington, Gen. Pharmac. 19(1):55 (1988). These disorders include disorders associated with stereoypic behaviors and drug dependence. D1 antagonists have been shown to block cocaine and morphine dependent pleasure sensations making the compounds of the present invention useful in treating drug dependence. Furthermore, although the precise mechanisms involved in a variety of movement disorders are unknown, it is generally accepted that they all use the striatum as a final common pathway. The striatum contains the highest density of D1 receptors suggesting that movement disorders may be treated using D1 antagonists. Consequently, the compounds of the present invention have potential utility in treating movement disorders such as Parkinson's disease, Hunington's chorea and tardive dyskinesias. Additionally, D1 antagonists have potential utility as inhibitors of disorders associated with repetitive, stereotypic behavior such as Lesch-Nyhan disease.

The antidepressive method of the invention is identified, for example, by test procedures which measure a compound's effect on tetrabenazine (TBZ)-induced ptosis in mice or which measure a compound's effect on muricide activity in rats as discussed below.

ANTIDEPRESSANT POTENTIAL

Effects on Tetrabenazine (TBZ)-Induced Ptosis in Mice

Clinically active antidepressant drugs are known to block TBZ-induced ptosis in mice (Psychosomatic Medicine, Nodine and Moyer, Eds., Lea and Febiger, Philadelphia, 1962, pp 683-90). Activity in this test is used to predict anti-depressant activity in man.

Methods and Materials

Groups of 5 mice are administered test drugs followed 30 minutes later by ip injection of tetrabenazine, 30 mg/kg. Thirty minutes later, the degree of ptosis is evaluated. Percent blockade of each treated group is used to determine $ED_{50}$'s, defined as that dose which prevents ptosis in 50% of mice. $ED_{50}$'s and 95% confidence limits are calculated by probit analysis.

Effects on Muricidal Behavior in Rats

Blockade of muricidal (mouse-killing) behavior in rats is used as a measure of evaluating the antidepressant activity of drugs (Int. J. Neuro-pharmacol., 5, 405-11 (1966)).

Methods and Materials

Groups of 5 rats are administered test drug intraperitonielly and are tested 30 and 60 minutes later for presence of muricidal behavior. Percent blockade of each treated group using data obtained at both these time points is calculated and dose-response data are used to determine each $ED_{50}$. $ED_{50}$ is defined as that dose which blocks muricide behavior in 50% of treated rats and is calculated using probit analysis.

The analgesic effect of the compounds of formula I and the method for providing analgesia may be exemplified by the Acetic Acid Writhing Test in Mice described below.

Acetic Acid Writhing Test in Mice

The blockade of writhing induced by the intraperitoneal injection of acetic acid is an established experimental animal model for the screening of antinociceptive drugs (drugs which prevent the appreciation or transmission of pain sensations). See Hendershot et al., *J. Pharmacol. Exp. Therap.* 125:237, (1959) and Koster et al., *Fed. Proc.* 18:412, (1959).

Methods and Materials

Compounds to be tested are dissolved or suspended in aqueous 0.4% methylcellulose vehicle. For oral administration, dosages are prepared for delivery of the selected weight of compound in a total volume of 20 mg/kg of body weight. For subcutaneous or intraperitoneal administration, dosages are prepared for delivery of the selected weight of compound in a volume of 10 ml/kg of body weight.

The test procedure is that described by Hendershot et al., supra, except that acetic acid is substituted for phenylquinone. Groups of five male CF1 mice (20–26 g.) are dosed orally with test drug and injected 15 minutes later with 0.6% aqueous acetic acid (10 mg/kg). The mice are placed in a large observation beaker and the number of writhes for each animal is counted during a 10 minute interval starting 3 minutes after injection of acetic acid. A writhe is defined as a sequence of arching of the back, pelvic rotation and hindlimb extension. Initial screening is performed using a dosage of 30 mg/kg. If this dose affords 50% or greater reduction in the number of writhes compared to the control, the animal is considered to be protected, a dose response curve is developed using a logarithmic sequence of lower doses and an $ED_{50}$ is determined by interpolation.

The renal vasodilation effect of compounds of formula I wherein X and Y are both hydroxy and R is hydrogen (i.e., the other substituents, e.g., $R^1$, Q, m and n can be varied as described above) can be demonstrated by test procedures which measure renal arterial blood flow, such as that described by McNay et al., *J. Pharmacol. and Exptl. Therap.* 151, 23 (1966), or which measure renal vascular resistance, such as that described by Weinstock et al., *J. Med. Chem.* 23, 973 (1980).

ANTI-AGGRESSIVE POTENTIAL

Anti-aggressive activity potential of the drugs can be evaluated by observing the tranquilizing activity of the compounds to be tested, e.g., in rhesus monkeys and other aggressive primates.

Methods and Materials

Administer test drugs at randomly log-spaced doses to four (4) rhesus monkeys and evaluate the tranquilizing activity at 0.5, 1, 2 and 4 hours after such administration. Use a rating scale in which animal behavior is scored as follows: indifferent (1–3), withdrawn (4–6), threatening (7–9), or attacking (10–12). Repeat the scoring procedure four (4) times: when the observer approaches, claps hands, rattles the animal's cage and opens the cage door. Compare the total scores for each animal under control or drug conditions to assess reduction in aggression.

In general, anti-anxiety compounds also demonstrate anti-aggressive activity. It is thus likely that compounds that show anti-aggressive potential will also have anti-anxiety potential and such anti-anxiety activity for the claimed compounds is expected.

For preparing pharmaceutical compositions from the compounds of formula I, inert, pharmaceutically acceptable carriers are admixed with the active compounds. The pharmaceutically acceptable carriers may be either solid or liquid. Solid form preparations include powders, tablets, dispersible granules, capsules, cachets and suppositories. A solid carrier can be one or more substances which may also act as diluents, flavoring agents, solubilizers, lubricants, suspending agents, binders or tablet disintegrating agents; it may also be an encapsulating material. In powders, the carrier is a finely divided solid which is in admixture with the finely divided active compound. In the tablet, the active compound is mixed with a carrier having the necessary binding properties in suitable proportions and compacted in the shape and size desired. The powders and tablets typically contain from 5 to about 70% of the active ingredient dependent upon the potency of the active compound, the size and age of the intended user, and the range of dosage required for the specific therapy. Suitable solid carriers are magnesium carbonate, magnesium stearate, talc, sugar, lactose, pectin, dextrin, starch, gelatin, tragacanth, methylcellulose, sodium carboxymethylcellulose, a low melting wax, cocoa butter and other materials typically used in the pharmaceutical industries. The term "preparation" is intended to include the formulation of the active compound with encapsulating material as carrier, providing a capsule in which the active component (with or without other carriers) is surrounded by a carrier, which is thus in association with it. Similarly, cachets are included. Tablets, powders, cachets and capsules can be used as solid dosage forms suitable for oral administration.

For preparing suppositories, a low melting wax such as a mixture of fatty acid glycerides or cocoa butter is first melted and the active ingredient is dispersed homogeneously therein as by stirring. The molten homogeneous mixture is then poured into convenient sized molds, allowed to cool and thereby solidify.

Liquid form preparations include solutions, suspensions and emulsions. As an example may be mentioned water or water-propylene glycol solutions for parenteral injection. Liquid preparations can also be formulated in solution in aqueous polyethylene glycol solution. Aqueous solutions suitable for oral use can be prepared by adding the active component in water and adding suitable colorants, flavors, stabilizing, sweetening, solubilizing and thickening agents as desired. Aqueous suspensions suitable for oral use can be made by dispersing the finely divided active component in water with viscous material, i.e., natural or synthetic gums, resins, methylcellulose, sodium carboxymethylcellulose and other well-known suspending agents.

Also included are solid form preparations which are intended to be converted, shortly before use, to liquid form preparations for either oral or parenteral administration. Such liquid forms include solutions, suspensions and emulsions. These particular solid form preparations are most conveniently provided in unit dose form and as such are used to provide a single liquid dosage unit. Alternatively, sufficient solid may be provided so that after conversion to liquid form, multiple individual liquid doses may be obtained by measuring predetermined volumes of the liquid form preparation as with a syringe, teaspoon or other volumetric container. The solid form preparations intended to be converted to liquid form may contain, in addition to the active material, flavorants, colorants, stabilizers, buffers, artificial and natural sweetners, dispersants, thickeners, solubilizing agents and the like. The solvent utilized for preparing the liquid form preparation may be water, isotonic aqueous salt solutions, ethanol, glycerine, propylene glycol and the like, as well as mixtures thereof. The solvent utilized will be chosen with regard to the route of administration. For example, liquid preparations containing large amounts of ethanol are not generally suitable for parenteral use.

The invention also contemplates alternative delivery systems including, but not necessarily limited to, transdermal delivery. The transdermal compositions can take the form of creams, lotions and/or emulsions and can be included in a transdermal patch of the matrix or reservoir type as are conventional in the art for this purpose.

A particularly useful dosage form is depot administration, which promotes a prolonged effect of the drug by sustaining the release of the drug. Such depot formulations comprise the formulation of the active ingredient into aqueous suspensions or in oil-based vehicles.

Preferably, the pharmaceutical preparation is in unit dosage form. In such form, the preparation is subdivided into unit doses containing appropriate quantities of the active components. The unit dosage form can be a packaged preparation, the package containing discrete quantities of preparation such as packeted tablets, capsules and powders in vials or ampules. The unit dosage form can also be a capsule, cachet or tablet itself, or it may be the appropriate number of any of these in a packaged form.

The quantity of active compound in a unit dose preparation may be varied or adjusted from 1 mg to 500 mg, preferably to 100 mg according to the particular application and the potency of the active ingredient and the intended treatment. This would correspond to a dose of about 0.02 to about 10 mg/kg, preferably to about 2.0 mg/kg which may be divided over 1 to 3 administrations per day. The composition may, if desired, also contain other therapeutic agents.

The dosages may be varied depending on the requirement of the patient, the severity of the condition being treating and the particular compound being employed. Determination of the proper dosage for a particular situation is within the skill of those in the medical art. For convenience, the total daily dosage may be divided and administered in portions throughout the day or by means providing continuous delivery.

The invention disclosed herein is exemplified by the following preparative examples which should not be construed to limit the scope of the disclosure. Alternative mechanistic pathways and analogous structures within the scope of applicants' invention may be apparent to those skilled in the art.

EXAMPLE 1

(a)

cis/trans-N-Methyl-N-(β-3,4-dimethoxyphenylethyl)-2-amino-1,2,3,4-tetrahydro-1-naphthol To a stirred solution of 94.0 g of N-methylhomoveratryl amine and 70 g of anhydrous potassium carbonate in 600 ml of dry dimethylformamide (DMF) was added in a period of 30 min. a solution of 108 g of 2-bromo-α-tetralone in 100 ml of dry DMF. The mixture was stirred at room temperature for 3 hours and then diluted with 5 liters of ice water. The mixture was extracted with 2×800 ml of ether and the combined ether extracts were washed with 2×500 ml of water. The residue resulting from evaporation of the dried ether layer was dissolved in 800 ml of anhydrous ethanol, was treated with 14.0 g of sodium borohydride (with cooling) and stirred for an additional 18 hours. After removing the solvent, the residue, in 500 ml of water, was heated on a steam bath for 30 min. After cooling, the aqueous mixture was extracted with 1 liter of ether. The ether layer was extracted with 700 ml of 1N HCl, and the acid extract was made slightly basic with sodium hydroxide and extracted with 1 liter of ether. Upon evaporation of the ether, the residue was chromatographed over silica gel to give cis/trans-N-methyl-N-(β-3,4-dimethoxyphenylethyl)-2-amino-1,2,3,4-tetrahydro-1-naphthol as a viscous gum.

(b)

cis/trans-6,7,7a,8,9,13b-Hexahydro-2,3-dimethoxy-7-methyl-5H-benzo[d]naphtho[2,1-b]azepine To 53.7 g of cis/trans-N-methyl-N-(β-3,4-dimethoxyphenylethyl)-2-amino-1,2,3,4-tetrahydro-1-naphthol was added 400 ml of anhydrous methanesulfonic acid with cooling and stirring. The mixture was stirred at room temperature for 4 additional hours, diluted with 2 liters of ice and water and made basic with 50% sodium hydroxide. The basic solution was chilled to 20° C. and then extracted with 500 ml of methylene chloride, followed by extraction with 500 ml of ether. Chromatography of the residue obtained by evaporation of the combined organic extracts over silica gel (ethyl acetate:ethanol:ammonium hydroxide, 100:3:1) afforded the cis isomer having a melting point of 114°-116° C. and the trans isomer as a colorless gum, the maleate derivative thereof having a melting point of 149°-152° C.

EXAMPLE 2 trans-6,7,7a,8,9,13b-Hexahydro-2-hydroxy-3-methoxy-7-methyl-5H-benzo[d]naphtho[2,1-b]azepine and trans-6,7,7a,8,9,13b-Hexahydro-3-hydroxy-2-methoxy-7-methyl-5H-benzo[d]naphtho[2,1-b]azepine To a stirred suspension of 6.1 g of 50% sodium hydride in 75 ml of dry DMF was added slowly a solution of 7.8 g of ethanethiol in 100 ml of dry DMF. After stirring for 20 min., a solution of 16.2 g of trans-6,7,7a,8,9,13b-hexahydro-2,3-dimethoxy-7-methyl-5H-benzo[d]naphtho[2,1-b]azepine in 75 ml of DMF was added over a period of 5 min. The mixture was heated slowly to reflux and maintained at reflux for 45 min. The heat source was removed and the reaction mixture was first chilled to 50° C. and then poured into 1.5 Kg of ice and water with stirring. The pH of the solution was adjusted to 8 by dropwise addition of acetic acid and the precipitate was removed by filtration. Fractional crystallization with, first chloroform-ethanol and then with acetonitrile, afforded trans-6,7,7a,8,9,13b-hexahydro-3-hydroxy-2-methoxy-7-methyl-5H-benzo[d]naphtho[2,1-b]azepine, m.p. 229°-231° C. and trans-6,7,7a,8,9,13b-hexahydro-2-hydroxy-3-methoxy-7-methyl-5H-benzo[d]naphtho[2,1-b]azepine, m.p. 194°-196° C.

EXAMPLE 3

(a)

trans-6,7,7a,8,9,13b-Hexahydro-2-methoxy-7-methyl-3-[5-(1-phenyl-1H-tetrazolyl)oxy]-5H-benzo[d]naphtho[2,1-b]azepine To a suspension of 5.2 g of trans-6,7,7a,8,9,13b-hexahydro-3-hydroxy-2-methoxy-7-methyl-5H-benzo[d-]naphtho[2,1-b]azepine in 40 ml of dry DMF was added, in small portions, 850 mg of 50% sodium hydride and the mixture was stirred for an additional 20 min. at room temperature. A solution of 3.18 g of 5-chlorophenyl-1H-tetrazole in 10 ml of DMF was added dropwise. After stirring for 2 hours at room temperature, the mixture was poured into 350 ml of ice and water. The solid obtained was recrystallized from ether to give trans-6,7,7a,8,9,13b-hexahydro-2-methoxy-7-methyl-3-[5-(1-phenyl-1H-tetrazolyl)oxy]-5H-benzo[d]naphtho[2,1-b]-6-azepine, m.p. 190°-192° C.

(b)

trans-6,7,7a,8,9,13b-Hexahydro-2-methoxy-7-methyl-5H-benzo[d]naphtho[2,1-b]azepine To a solution of 6.8 g of trans-6,7,7a,8,9,13b-hexahydro-2-methoxy-7-methyl-3-[5(1-phenyl-1H-tetrazolyl-)oxy]-5H-benzo[d]naphtho[2,1-b]azepine in 100 ml of acetic acid was added 750 mg of 20% palladium hydroxide on carbon. The resulting mixture was then hydrogenated at 60 psi at 55° C. for 5.5 hours. After removing both catalyst and solvent, the residue was treated with 150 ml of ether and 50 ml of 1N sodium hydroxide. The residue obtained from evaporation of the dried ether layer was recrystallized from ether to give trans-6,7,7a,8,9,13b-hexahydro-2-methoxy-7-methyl-5H-benzo[d]naphtho[2,1-b]azepine, m.p. 96°-98° C.

EXAMPLE 4 trans-6,7,7a,8,9,13b-Hexahydro-2-hydroxy-7-methyl-5H-benzo[d]naphtho[2,1-b]azepine To 2.0 g of trans-6,7,7a,8,9,13b-hexahydro-2-methoxy-7-methyl-5H-benzo[d]naphtho[2,1-b]azepine was added 20 ml of 48% hydrobromic acid and the mixture was heated in an oil bath at 130° C., with stirring, for 4.5 hours. The excess hydrobromic acid was distilled away and the residue was dissolved in 200 ml of boiling water. The pH of the hot aqueous solution was adjusted to 8 with sodium bicarbonate and the solution was cooled to 10° C. The precipitated solid was recrystallized from acetonitrile to afford trans-6,7,7a,8,9,13b-hexahydro-2-hydroxy-7-methyl-5H-benzo[d]naphtho[2,1-b]azepine, m.p. 209°-211° C.

EXAMPLE 5 trans-6,7,7a,8,9,13b-Hexahydro-3-chloro-2-hydroxy-7-methyl-5H-benzo[d]naphtho[2,1-b]azepine To a stirred suspension of 0.45 g each of trans-6,7,7a,8,9,13b-hexahydro-2-hydroxy-7-methyl-5H-benzo[d]naphtho[2,1-b]azepine and silica gel (60-200 mesh) in 30 ml of tetrahydrofuran was added 0.14 ml of sulfuryl chloride. The suspension was stirred for 20 min. at room temperature and the solvent removed at 25° C. by vacuum evaporation. The residue was treated with 10 ml of water and 30 ml of chloroform, and the pH was adjusted to 8 by addition of solid sodium bicarbonate. The organic layer was dried, filtered and evaporated to yield a gummy residue which was chromatographed on silica gel (chloroform:ethanol:ammonium hydroxide—100:4:1.5) to yield trans-6,7,7a,8,9,13b-hexahydro-3-chloro-2-hydroxy-7-methyl-5H-benzo[d]naphtho[2,1-b]azepine, m.p. 215°-216° C. after recrystallization from acetonitrile.

EXAMPLE 6

(a)

trans-6,7,7a,8,9,13b-Hexahydro-2-hydroxy-3-hydroxymethyl-7-methyl-5H-benzo[d]naphtho[2,1-b]azepine To a solution of 515 mg of trans-6,7,7a,8,9,13b-hexahydro-2-hydroxy-7-methyl-5H-benzo[d]naphtho[2,1-b]azepine in 7.0 ml each of dimethoxyethane and 3.3% of aqueous potassium hydroxide was added 0.6 ml of 37% formaldehyde and the reaction was stirred at 80° C. for 3.5 hours. The solvents were removed by evaporation and the resulting residue was dissolved in 20 ml of water. The pH of the aqueous solution was first adjusted to 8 by dropwise addition of acetic acid and then was extracted twice with 25 ml portions of chloroform. The residue obtained by evaporation of the organic layer was purified by chromatography on a silica gel column (chloroform:ethanol:ammonium hydroxide—50:3:1) to give trans-6,7,7a,8,9,13b-hexahydro-2-hydroxy-3-hydroxymethyl-7-methyl-5H-benzo[d]naphtho[2,1-b]azepine, as a colorless gum.

(b)

trans-6,7,7a,8,9,13b-Hexahydro-2-hydroxy-3,7-dimethyl-7-methyl-5H-benzo[d]naphtho[2,1-b]azepine To a solution of 500 mg of trans-6,7,7a,8,9,13b-hexahydro-2-hydroxy-3-hydroxymethyl-7-methyl-5H-benzo[d]naphtho[2,1-b]azepine and 0.6 g of p-toluenesulfonic acid monohydrate in 20 ml of glacial acetic acid was added 60 mg of 20% palladium hydroxide on carbon and the mixture was heated to 60° C. for 18 hours under a hydrogen atmosphere at a pressure of 60 psi (ca 4.2 kg/cm$^2$). After removal of catalyst and solvent, the residue was dissolved in 3 ml of DMF and then poured onto a stirred solution of 75 ml of 3% sodium bicarbonate. The solid was filtered and subsequently purified by chromatography on silica gel (chloroform:ethanol:ammonium hydroxide—50:3:1) to afford trans-6,7,7a,8,9,13b-hexahydro-2-hydroxy-3-methyl-7-methyl-5H-benzo[d]naphtho[2,1-b]azepine, m.p. 235°-237° C.

The stereochemistry of the above-described compounds was determined by nuclear magnetic resonance and the assignments confirmed on a selected compound, trans-6,7,7a,8,9,13b-hexahydro-2-hydroxy-3-methoxy-7-methyl-5H-benzo[d]naphtho[2,1-b]azepine, by X-ray crystallography.

EXAMPLE 7

(+)-trans-6,7,7a,8,9,13b-Hexahydro-3-chloro-2-methoxy-7-methyl-5H-benzo[d]naphtho[2,1-b]azepine A mixture of 2.70 g of trans-6,7,7a,8,9,13b-hexahydro-3-chloro-2-methoxy-7-methyl-5H-benzo[d]naphtho[2,1-b]azepine and 3.18 g of di-p-tolyl-d-tartaric acid in 35 ml of ethyl acetate was heated on a steambath. After initial dissolution, a solid formed. The mixture was cooled to room temperature and the precipitated solids filtered. The wet filtered solids were digested for 10 minutes with 50 ml ethanol on a steambath, the mixture cooled, and solids filtered. This material was dissolved in 75 ml of 95% ethanol with heating. The solution was poured into a beaker and allowed to evaporate slowly at room temperature to 50 ml. Solids were filtered and washed with cold ethanol to give 2.5 g product, m.p. 173°-175° C. This was redissolved in 100 ml of 95% ethanol, and the resulting solution allowed to slowly partially evaporate. The solids formed were filtered to give 462 mg of the title compound as the tartarate salt, m.p. 188°-189° C.

This material was dissolved in water and treated with aqueous NaOH to give the title compound as the free base, which is a syrup, $[\alpha]_D^{25}$ 209.1 (C 1.25, $C_2H_5OH$).

EXAMPLE 8

(+)-trans-6,7,7a,8,9,13b-hexahydro-3-chloro-2-hydroxy-7-methyl-5H-benzo[d]naphtho[2,1-b]azepine 190 mg of (+)-trans-6,7,7a,8,9,13b-hexahydro-3-chloro-2-methoxy-7-methyl-5H-benzo[d]naphtho[2,1-b]azepine was heated in a mixture of 2 ml each of 48% HBr and 2 ml of acetic acid for 5½ hrs. The mixture was evaporated almost to dryness at 120° C. in vacuo and 5 ml of water added to the residue, which was then heated on a steam bath for 5 minutes. The aqueous solution then poured into a solution of 2 g of $NaHCO_3$ in 40 ml of $H_2O$. The insoluble residue was taken up in hot dimethylformamide (DMF) and added to the $NaHCO_3$ solution as well. Precipitated material was filtered off, washed with water and air-dried.

Recrystallization from acetonitrile gave 130 mg of the title compound, m.p. 239°-241°, $[\alpha]_D^{25}$ 220.5 (C 0.29, DMF).

EXAMPLE 9

(−)-trans-6,7,7a,8,9,13b-Hexahydro-3-chloro-2-methoxy-7-methyl-5H-benzo[d]naphtho[2,1-b]azepine By basically the same procedure as described in Example 7 above but using di-p-tolyl-L-tartaric acid, one obtains the title compound as the tartarate salt, m.p. 188°-189° C., which gave the oily base, $[\alpha]_D^{25}-204.9$ (C 1.17, $C_2H_5OH$), on treatment with aqueous NaOH.

EXAMPLE 10

(−)-trans-6,7,7a,8,9,13b-Hexahydro-3-chloro-2-hydroxy-7-methyl-5H-benzo[b]naphtho[2,1-b]azepine From (−)-trans-6,7,7a,8,9,13b-hexahydro-3-chloro-2-methoxy-7-methyl-5H-benzo[d]naphtho[2,1-b]azepine in a manner analogous to that described in Example 8 above, one obtains the title compound, m.p. 239°-41° C., $[\alpha]_D^{25}-235°/1°$ (C 0.295, DMF).

EXAMPLE 11

(a) 1-(3-Methoxyphenyl)-3,4-dihydronaphthalene

A solution of the Grignard reagent derived from 50 g (0.27 mol) of 3-bromoanisole in 200 ml of dry THF was treated with a solution of alpha-tetralone in 100 ml of THF added over 1 hour while maintaining the internal temperature at 15°-25° C. After stirring overnight, the mixture was diluted with 500 ml of ether and quenched with 200 ml of 20% aqueous ammonium chloride. The aqueous layer was extracted with 200 ml of ether. The combined organic layers were dried over $MgSO_4$ and evaporated to 66.5 g of the oily alcohol. This was dissolved in 450 ml of dry toluene containing 0.020 g of p-toluenesulfonic acid and refluxed overnight in a Dean-Stark apparatus. After cooling, the mixture was washed with 100 ml of 5% sodium bicarbonate, with 100 ml of water, and then with 100 ml of brine. The mixture was dried over $MgSO_4$ and evaporated. The residue was distilled under reduced pressure to give the title compound, b.p. (0.5 mm) 158°-162° C.

(b)

1-(3-Methoxyphenyl)-2-oxo-1,2,3,4-tetrahydronaphthalene

To a 2-phase mixture of 25.1 g (0.106 mol) of 1-(3-methoxyphenyl)-3,4-dihydronaphthalene, 20 g (0.238 mol) of sodium bicarbonate, 200 ml of water, and 400 ml of methylene chloride at 5° C. was added 24.4 g of 80-85% m-chloroperbenzoic acid portion-wise over 15 minutes. The internal temperature rose to 10° C. After the addition was complete, the mixture was stirred at 0°-5° C. for 2 hr. The layers were separated and the aqueous layer was extracted with 100 ml of methylene chloride. The combined organic layers were extracted with 200 ml of 10% sodium carbonate and then with 100 ml of water, dried over $MgSO_4$ and evaporated to an oil. IR, NMR, and thin layer chromatography indicated the presence of a mixture of epoxide and 1,2-diol monoester. The crude mixture was stirred 3 hours at room temperature in 1M solution of sodium hydroxide in 5:1 ethanol-water. After adjusting the pH to 8 with HCl, the bulk of the solvent was evaporated. The residue was taken up in 500 ml of ether, which was then washed with 50 ml of water, dried over $MgSO_4$, and evaporated. The oily residue was dissolved in 300 ml of dry toluene containing 0.050 g of p-toluenesulfonic acid and refluxed 3 hour in a Dean-Stark apparatus. The solution was washed with 50 ml of 5% sodium bicarbonate and with 50 ml of water, dried over $MgSO_4$ and evaporated to give 25.1 g of the title compound, which was characterized as its 2,4-dinitrophenyl hydrazone derivative, m.p. 161°-161.5° C. (ethanol).

(c)

1-(3-Methoxyphenyl)-2-(N-methylamino)-3,4-dihydronaphthalene

Dry methylamine gas was bubbled through a refluxing solution of 18.0 g of 1-(3-methoxyphenyl)-2-oxo-1,2,3,4-tetrahydyronaphthalene in 300 ml of toluene in a Dean-Stark apparatus. After 1.5 hour the mixture was cooled and evaporated to give the title compound as a semi-solid enamine which was characterized by NMR δ2.70 (S,3H), 2.3-3.0 (M,4H), 3.80 (S,3H), 6.7-7.5 (M,8H).

(d)

cis-1-(3-Methoxyphenyl)-2-(N-methylamino)-1,2,3,4-tetrahydronaphthalene

Zinc dust (21 g, 321 mol) was activated by washing with 1M HCl, water, methanol, and ether, and then drying in vacuo. To the suspension of zinc dust in 300 ml of glacial acetic acid was added 17.0 g of 1-(3-methoxyphenyl)-2-(N-methylamino)-3,4-dihydronaphthalene, and the mixture was stirred at 100° C. for 16 hrs. The mixture was cooled, filtered, and evaporated to dryness. The residue was dissolved in 100 ml of 0.5M HCl and extracted with 100 ml of ether. The aqueous layer was made strongly basic with solid KOH, then extracted twice with 300 ml of ethyl acetate. The ethyl acetate was dried over $MgSO_4$ and evaporated to an oil which was transformed into its HCl salt by ethereal HCl to provide the title compound as its hydrochloride salt, m.p. 172°-174° C.

(e)

trans-1-(3-Methoxyphenyl)-2-(N-methylamino)-1,2,3,4-tetrahydronaphthalene

The cis-amine prepared in Example 11(d) above was dissolved in 300 ml of dry dimethylsulfoxide (DMSO). To this was added 15 g (0.134 mol) of potassium t-butoxide portion-wise over 30 minutes. The mixture was stirred at room temperature for an additional 2 hrs., then poured into 300 ml of 10% sodium bicarbonate. The resulting mixture was extracted three times with 300 ml of ether. The ether layer was washed three times with 300 ml of water, dried over $MgSO_4$, and evaporated to give 13.1 g of the title compound slightly contaminated with the cis-amine (3%). This was characterized by NMR:

| PPM | | | |
|---|---|---|---|
| cis | | trans | |
| 2.55 | (S, 3H) | 2.32 | (S, 3H) |
| 2.8-3.8 | (M, 5H) | 2.6-3.2 | (M, 5H) |
| 3.80 | (S, 3H) | 3.70 | (S, 3H) |
| 4.36 | (D, 1H, J=5Hz) | 3.82 | (D, 1H, J=Hz) |
| 6.5-7.3 | (M, 3H) | 6.5-7.5 | (M, 8H) |

(f)

trans-1-(3-Methoxyphenyl)-2-(N-chloroacetyl-N-methylamino)-1,2,3,4-tetrahydronaphthalene 8.7 g of the trans compound of Example 11(e) above (0.032 mol) was dissolved in 100 ml of methylene chloride. To this was added 4.9 g (0.036 mol) of potassium carbonate in 30 ml of water followed by 2.9 ml (0.036 mol) of chloroacetyl chloride added dropwise over 5 minutes with vigorous stirring. After 2 hrs., the mixture was diluted with 300 ml of ethyl acetate. The aqueous layer was extracted with 50 ml of ethyl acetate. The combined organic layers were washed with 50 ml of 1M HCl and with 50 ml of water, dried over $MgSO_4$ and evaporated to the title compound as a chromatographically and spectroscopically pure oil, 11.0 g, which was characterized by IR: 1655 $cm^{-1}$.

(g)

trans-6,7,7a,8,9,13b-hexahydro-2-methoxy-7-methyl-5H-benzo[d]naphtho[2,1-b]azepine

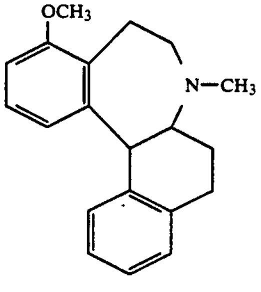

A

-continued

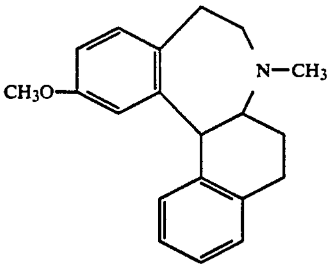

B

A solution of 2.8 g of the compound of Example 11(f) above in 400 ml of 60:40 ml of ethanol-water was irradiated with a 400 W Hanovia lamp with Vycor filter for 3 hrs. at room temperature in a nitrogen atmosphere. The pH of the solution was adjusted to pH 8 with aqueous sodium carbonate and the solvent was evaporated. The residue was taken up in 300 ml of ethyl acetate, washed with 50 ml of water, dried over $MgSO_4$ and evaporated to a semi-solid. Chromatography on silica gel eluting with 30% ethyl acetate hexane gave 300 mg of the 9-methoxy derivative of formula A above and 370 mg of the desired 7-methoxy derivative of formula B above.

A portion of the 7-methoxy compound of formula B above was treated with excess borane-THF to give the title compound whose NMR and TLC behavior were identical with a fully characterized sample prepared by a different route.

EXAMPLE 12

(a) 4-(3-Methoxyphenyl)-$\Delta^{3,4}$-chromene

A solution of 3-methoxyphenyl magnesium bromide was prepared by adding 27.7 g of m-bromoanisole to a suspension of magnesium turnings (3.6 g) in 150 ml of tetrahydrofuran (THF) dropwise over 1 hr. The mixture was heated at reflux for 2 hrs. The resulting solution was cooled to 5° C. and a solution of 4-chromanone (20.0 g) in 50 ml of dry THF added over 2 hrs. at 15° C. The resulting mixture was stirred overnight at room temperature, cooled to 10° C., and treated with 1N HCl until pH 7 was reached. The mixture was diluted with water, extracted twice with 500 ml of ether, and the combined extracts dried over $MgSO_4$. Filtration and evaporation gave 29.6 g of the title compound as an oil. NMR ($CDCl_3$); δ3.81 (S,3H), 4.80 (d,J=4 Hz, 2H) 5.76 (t,J=4 Hz, 1H), 6.7-7.4 (M,8H).

(b) 4-(3-Methoxyphenyl)-chroman-2-one m-Chloroperbenzoic acid (25.2 g, 80.85% pure) was added portionwise over 3 minutes to a stirred mixture of the title compound of Example 12(a) above (29.6 g) in 200 ml of $H_2O$, 23 g $NaHCO_3$ and 400 ml of $CH_2Cl_2$ at 5°-10° C. Stirring was continued at 5°-10° C. for 3 hrs., the organic layer was separated, and the aqueous layer was extracted with 200 ml of $CH_2Cl_2$. The extracts were combined with the original organic layer and dried over $MgSO_4$. Filtration and evaporation of solvent gave a product which was dissolved in 200 ml of 1M NaOH in 3:1 ethanol-water and stirred at room temperature for 2 hrs. The pH was then brought to 9 with HCl, and most of the solvemt was evaporated. The aqueous residue was extracted three times with 200 ml of portions of ether. The combined extracts were dried over $MgSO_4$, filtered and evaporated. The oily residue was taken up in 400 ml of toluene containing 0.5 g of p-toluene sulfonic acid and the solution was heated at reflux for 2 hrs. On cooling, the solution was washed with 100 ml of 0.5M $NaHCO_3$, dried over $MgSO_4$ and evaporated. The residue was chromatographed on silica gel eluting with toluene to give 10.3 g of the title compound as an oil. NMR ($CDCl_3$); δ3.73 (S,3H), 4.49 (Br.s, 2H), 4.70 (Br.s, 1H) 6.65–7.66 (M, 8H).

(c)
4-(m-Methoxyphenyl)-3-methylamino-$\Delta^{3,4}$-chromene

A stream of anhydrous methylamine gas was passed through a refluxing solution of 5.4 g of the title compound of Example 12(b) above in 200 ml of dry toluene for 1½ hr. until water evolution ceased. Cooling and evaporation gave 5.45 g of the title compound as an oil. NMR ($CDCl_3$) δ2.63 (S,3H), 3.77 (S,3H), 4.83 (S,2H) 6.40–7.62 (M,8H).

(d)
trans-4-(m-Methoxyphenyl)-3-methylamino-chroman

Sodium cyanoborohydride (1.27 g) was added to a mixture of the title compound of Example 12(c) above (5.4 g) in 400 ml of absolute alcohol followed by addition of 1.2 ml of glacial acetic acid. After stirring overnight at room temperature under a nitrogen atmosphere, 60 ml of 1M HCl was added and stirring continued for 30 minutes. The bulk of the solvent was then evaporated, and the residue partitioned between 300 ml ether and 300 ml water. The aqueous layer was separated and washed with 100 ml of ether. The pH adjusted to 8–10 with solid KOH. This mixture was then extracted three times with 300 ml portions of ether, which were combined, dried, and evaporated to give 4.35 g an oily product.

4.0 g of this last material was dissolved in a mixture of 100 ml of dimethylsulfoxide (DMSO) and 25 ml of dimethylformamide (DMF), cooled to about 0° C., and potassium t-butoxide (5.0 g) was added portion-wise over 5 more minutes. The mixture was then diluted with 100 ml of ice water followed by 5.0 g solid $NaHCO_3$. The resulting mixture was then poured into 400 ml of ether, and the organic layer separated. The aqueous layer was extracted with 400 ml ether, combined with the initial ether phase and washed twice with 100 ml portions of water. Drying over $MgSO_4$, filtration, and evaporation of solvent gave 3.9 g of the title compound as an oil. NMR Spectrum ($CDCl_3$), δ2.48 (S,3H), 3.05 (M,1H), 3.77 (S,3H), 3.96 (dd,1H,J=7 Hz, 11 Hz), 4.26 (dd, 1H,J=3 Hz,11 Hz), 6.65–7.30 (M,8H).

(e)
trans-3-[N-(2,2-Diethoxyethyl)-N-methylamino[-4-(3-methoxyphenyl)-chroman

A mixture of the title compound of Example 12(d) above (3.54 g), bromoacetaldehyde diethylacetal (4.0 ml), KI (0.33 g), $K_2CO_3$ (4.0 g) and dry dimethylformamide (150 ml) was heated at 155° C. under a nitrogen atmosphere for 10 hrs., then allowed to stand at room temperature overnight. The mixture was then diluted with 700 ml of ether and washed three times with 150 ml portions of water. The organic layer was dried over $MgSO_4$, filtered, and evaporated in high vacuum to give 5.1 g the title compound as an oil. NMR Spectrum ($CDCl_3$): δ1.11 (M,6H), 2.43 (S,3H), 2.69 (d,J=6 Hz, 2H), 3.11 (M,1H), 3.3–3.7 (M,4h), 3.76 (S,3H), 4.05–4.30 (M,3H), 4.35 (t,1H,J=6 Hz), 6.65–6.90 (M,6H), 7.05–7.25 (M,2H).

(f)
trans-6,6a,7,8,9,13b-Hexahydro-12-methoxy-7-methyl[1]benzopyrano[4,3-a][3]benzazepine To 250 ml of 18N sulfuric acid at 0° C. was added 5.0 g of the title compound of Example 12(e) above. The heterogeneous mixture was stirred vigorously while coming to room temperature overnight. The now homogeneous mixture was poured over crushed ice. With continuous vigorous stirring and cooling via an ice bath, the pH was raised to 8–10 by slow addition of 50% NaOH over 3 hrs. The mixture was extracted three times, with 500 ml of ethyl acetate, dried over magnesium sulfate, and evaporated to give 3.6 g crude oil. This material was dissolved in 200 ml of ethyl acetate and hydrogenated over 5% palladium on carbon at 50 psi. After filtration, the mixture was separated by HPLC on silica gel eluting with ethyl acetate to give 219 mg of the title compound. NMR ($CDCl_3$): δ2.45 (S,3H), 2.49–2.98 (M,4H), 3.14 (M,1H), 3.59 (S,3H), 3.7 (dd,J=10 Hz, 11 Hz, 1H), 4.39 (dd,1H,J=10 Hz,5 Hz), 4.74 (d,1H-J=7.6 Hz), 6.02 (d,1H,J=1.6 Hz), 6.56 (dd,1H,J=8 Hz,2.6 Hz), 6.83–7.31 (M,5H).

EXAMPLE 13 trans-6,6a,7,8,9,13b-Hexahydro-7-methyl[1]benzopyrano[4,3-a][3]benzazepin-12-ol

A solution of the title compound from Example 12(f) above (330 mg) in 15 ml of $CH_2Cl_2$ was cooled to −78° C. and $BBr_3$ (132 μl) added dropwise over 1 minute. The mixture was allowed to come to room temperature and was stirred for 23 hrs. under nitrogen. Methanol (5 ml) were then added and the mixture stirred for 10 minutes, after which it was evaporated to dryness. The methanol treatment was repeated, after which the mixture was evaporated in high vacuum to give 400 mg solids. These solids were dissolved in ethanol and the solution treated with decolorizing carbon at reflux. Filtration and evaporation gave 240 mg of the title compound, m.p. 223°–226° C.

EXAMPLE 14

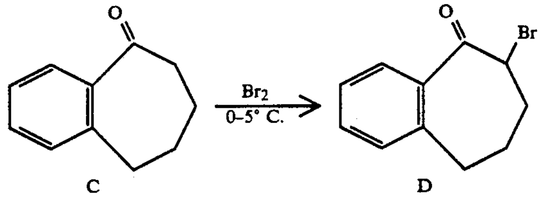

C D

A. To a stirred solution of 50.0 g of 1-benzosuberone (Compound C above) in 900 ml of ether was added 1 ml of $Br_2$ at −5° C. with stirring. The mixture was allowed to come to 5° C. slowly with stirring. The brown color disappeared at once at this temperature. $Br_2$ (15 ml) was then added dropwisely at 5° C. with stirring. The reaction mixture was extracted twice with one liter of ice water, once with 500 ml of saturated $NaHCO_3$ (with caution), then finally with 500 ml of ice water. The organic layer was dried over $Na_2SO_4$, filtered and then distilled down to the dryness. 75.20 g of viscous syrup was obtained, which was a compound of formula D above as confirmed by NMR.

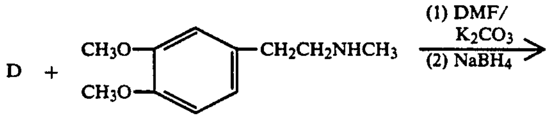

E

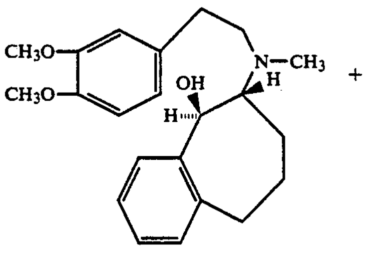

Fb

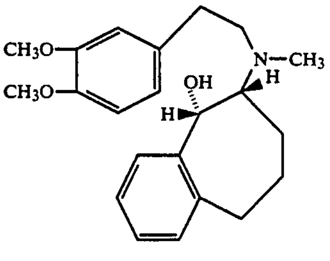

Fa

B. A mixture of 75.0 g of a compound of formula D above, 60 g of a compound of formula E, and 100 g of anhydrous $K_2CO_3$ in 400 ml of DMF was stirred at room temperature for 3½ hours. The mixture was diluted with 3.5 liters of ice water and extracted twice with 800 ml of ether. The ether layers were combined and washed twice with 1 liter of ice water, dried over $Na_2SO_4$, filtered and distilled down to the dryness on a steam bath. The residue was dissolved in one liter of ethanol. This solution was chilled in an ice bath. 7.0 g of $NaBH_4$ was added in small portions with stirring. After addition, the ice bath was removed and the reaction mixture was stirred at room temperature overnight. The mixture was distilled down to the dryness on a steam bath under house vacuum. The residue with 400 ml of water was heated on a steam bath with occasional stirring for 30 minutes, chilled to 15° C. and extracted twice with 300 ml of ether. The combined ether layers were extracted twice with 250 ml of 1N HCl. This aqueous acidic layer was made basic with NaOH and then extracted twice with 300 ml of ether. 28.10 g of an oily syrup was obtained from the ether layers, and was purified through a column of 500 g of T.L.C. grade silica gel, eluting with chloroform: ethanol:aqueous ammonia (100/3/1), which provided 9.2 g of the compound of formula Fa as an oily syrup and 4.5 g of the compound of formula Fb as a solid, m.p. 141°-143° C.

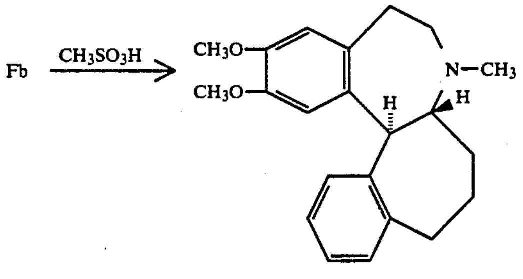

G

C. 4.50 g of the compound of formula Fb above was added in small portions to 35 ml of methanesulfonic acid at 15° C. with stirring. The stirring was continued at room temperature for four hours longer. The mixture was poured into 200 ml of ice and $H_2O$, made basic with 50% NaOH and then extracted twice with 125 ml of ether. The ether layers were combined, dried over $K_2CO_3$, filtered and evaporated down to the dryness to provide 3.95 g of a viscous syrup. This material was crystallized from isopropyl ether to provide 2.7 g of a solid of formula G above, m.p. 76°-78° C.

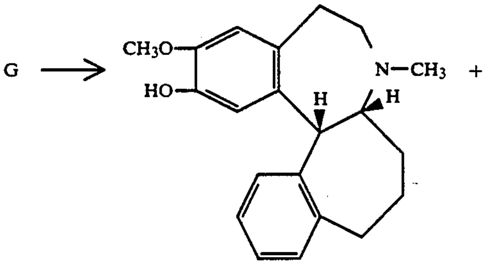

H

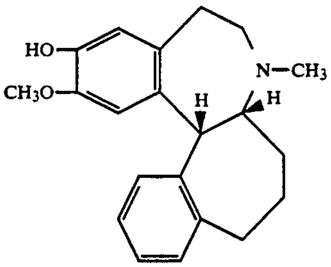

J

D. 2.0 g of ethanethiol in 25 ml of dry DMF was added slowly to a stirred suspension of 1.50 g of 50% NaH in 20 ml of DMF (under $N_2$ and a chlorox trap). After 20 minutes a solution of 4.0 g of a compound of formula G above in 20 ml of DMF was added in a period of five minutes. The mixture was maintained at 135° C. for one hour with stirring and then at 145° C. for 25 minutes longer. The mixture was chilled to about 50° C. and poured into 400 g of ice and $H_2O$. Acetic acid was added dropwise with stirring until a pH of about 8 was reached. A gummy precipitate was filtered and air dried. This material was dissolved in 30 ml of $CHCl_3$ and a solid crystallized out partially standing. The mother liquor was reserved for the treatment described in the next paragraph below. The solid was filtered and recrystallized from acetonitrile. The solid obtained was dried under vacuum for 3 hours to provide 900 mg of a compound of formula H above, m.p. 190°-192° C.

The residue obtained by evaporation of mother liquor from the filtration was placed onto a column containing 120 g of TLC grade silica gel and eluted with chloroform:ethanol:aqueous ammonia (100:35:10). The fractions containing mostly the desired material were combined. The solvent was removed to give 320 mg of an oily residue. This residue was used to prepare a maleate salt with 116 mg of maleic acid and ethylacetate/ethanol as solvent to provide 160 mg of the desired compound of formula J above as the maleate salt, m.p. 188°-190° C.

EXAMPLE 15 trans-5,6,7,7a,8,12b-Hexahydro-2-hydroxy-3-chloro-7-methyl-benz[d]indeno[2,1-b]azepine

A. 1-(3-Methoxy-4-chlorophenyl)-1-indene

Into a 500 mL three-neck flask fitted with a reflux condenser and addition funnel was placed 4.6 gm (0.189 mmol) magnesium ribbon and one crystal of iodine. The flask was flushed with dry nitrogen while heating briefly with a flame. After cooling, 25 mL of a solution of 38.0 gm (0.172 mmol) 2-chloro-5-bromoanisole in 200 mL dry ether was added from the addition funnel, and the flask was warmed briefly to initiate reaction. Thereafter, the solution was added over the course of one hour at a rate which maintained a gentle reflux. When the addition was complete, the reaction was heated to reflux for an additional three hours. The flask was cooled in an ice-salt bath to 0° C., and a solution of 1-indanone in 100 mL dry ether was added over 90 minutes while maintaining the reaction temperature at less than 10 degrees. Thereafter, the reaction was stirred at room temperature overnight, then quenched with 1M aqueous HCl until pH7. The aqueous layer was separated and extracted twice with 200 mL ether. The combined ether layers were dried ($MgSO_4$) and evaporated to an oil. This was purified by HPLC, eluting with 5% ethyl actetate in hexane to give 23.4 grams of 1-(3-methoxy-4-chlorophenyl)-1-indene (Compound K), 200 MHz NMR($CDCl_3$) d 3.51(d,2H,J=2 Hz), 3.95(s,3H), 6.59(tr,1H,J=2 Hz), 6.85-7.58(m,7H).

B. trans-1-(3-Methoxy-4-chlorophenyl)-2-indanamine

A solution of 17.9 grams (69.7 mmol) of the Compound K from step A dissolved in 70 mL dry diglyme was treated with 11.6 mL of 2M borane-methyl sulfide complex in methylene chloride, and the mixture was stirred at 65° C. for 24 hours. A solution of 8.13 grams (71.8 mmol) hydroxylamine O-sulfonic acid in 50 mL dry diglyme was added, and stirring was continued at 100° C. for 6 hours. After cooling to room temperature, the reaction was quenched with 3N HCl until acidic, then stirred for two hours. The reaction was diluted with 300 mL water and extracted three times with 200 mL ethyl acetate. The aqueous layer was made basic with solid potassium hydroxide and extracted three times with 300 mL ethyl actetate. The organic layer was dried ($MgSO_4$) and evaporated. The residue was filtered through a silica gel column, eluting first with hexane and then with 10% methanol-methylene chloride to give 5.47 grams (28%) of trans-1-(3-methoxy-4-chlorophenyl)-2-indanamine (Compound L), 200 MHz NMR ($CDCl_3$) d 2.76(dd,1H,J=9,16 Hz), 3.24(dd,1H,J=8,16 Hz),3.86 (d,1H,J=8 Hz), 6.70-6.90(m,3H),7.10-7.30(m,4H).

C. N-(2,2-diethoxyethyl)-trans-1-(3-Methoxy-4-chlorophenyl)-2-indanamine

A mixture of 1.0 grams(3.65 mmol) of Compound L from step B, 0.55 mL (3.65 mmol) 2-bromoacetaldehyde diethyl acetal, and 1.0 grams (7.3 mmol) anhydrous potassium carbonate in 35 mL dry DMF was stirred at 150° C. for 4 hours. After cooling to room temperature, the mixture was poured into 300 mL ether, washed with three 50 mL portions of water, dried ($MgSO_4$) and evaporated. The residue was purified by flash chromatography, eluting with 1:1 hexane-ethyl acetate to give 1.1 grams (77%) of N-(2,2-diethoxyethyl)-trans-1-(3-methoxy-4-chlorophenyl-2-indanamine (Compound M) as an oil, 200 MHz NMR($CDCl_3$) d 1.15(tr,6H,J=7 Hz), 2.70-290(m,3H), 3.20-3.70(m,6H), 4.09(d,1H,J=8 Hz), 4.55(tr,1H,J=5 Hz), 6.70-6.90(m,3H), 7.10-7.30(m,4H).

D. trans-7,7a,8,12b-tetrahydro-2-methoxy-3-chlorobenz[d]indeno[2,1-b]azepine A solution of Compound M from step C dissolved in 100 mL methylene chloride at 0° C. was treated with 100 mL trifluoromethanesulfonic acid added in a slow steady stream over 10 minutes. The mixture was stirred for five hours while coming to room temperature. The mixture was again cooled to 0° C. and cautiously quenched with saturated aqueous sodium bicarbonate until pH7. The mixture was extracted with three 100 mL portions of methylene chloride. The organic layer was dried ($MgSO_4$) and evaporated to give 0.57 grams of trans-7,7a,8,12b-tetrahydro-2-methoxy-3-chlorobenz[d]indeno[2,1-b]azepine (Compound N) as a dark oil, 200 MHz NMR ($CDCl_3$) d 2.79(dd,1H,J=8 Hz,15 Hz), 3.50-3.59(m,2H), 3.78(s,3H), 4.27(d,1H,J=6 Hz), 5.21(d,1H,J=10 Hz), 6.23(dd,1H,J=5,10 Hz), 6.99(s,1H), 7.18(s,1H), 7.20-7.55(m,4H).

E. trans-5,6,7,7a,8,12b-hexahydro-2-methoxy-3-chlorobenz[d]indeno[2,1-b]azepine The crude Compound N from step D was dissolved in 20 mL absolute ethanol and treated with 0.12 grams (1.91 mmol) sodium cyanoborohydride. To this was added 0.108 mL glacial acetic acid, and the mixture was stirred at room temperature for 3 hours. The reaction was quenched with 10 mL 1M HCl and stirred for 30 minutes. The reaction was made basic with 30% NaOH and extracted into 250 mL ethyl actetate. The organic layer was dried ($MgSO_4$) and evaporated to give 350 mg (53%) of trans-5,6,7,7a,8,12b-hexahydro-2-methoxy-3-chlorobenz[d]indeno[2,1-b]azepine (Compound P) as an oil, 200 MHz NMR ($CDCl_3$) d 3.60-3.85(m,3H), 3.10-3.40(m,4H), 3.71(s,3H), 4.54(d,1H,J=8 Hz), 7.07(s,1H), 7.16(s,1H), 7.20-7.40(m,4H).

F. trans-5,6,7,7a,8,12b-Hexahydro-2-methoxy-3-chloro-7-methyl-benz[d]indeno[2,1-b]azepine A solution of 300 mg (1.00 mmol) of Compound P from step E was dissolved in 20 mL acetonitrile and 0.40 mL (5.3 mmol) 37% aqueous formaldehyde was added followed by 0.10 grams (1.59 mmol) sodium cyanoborohydride. After 30 minutes, the solution was brought to pH 7 by dropwise addition of glacial acetic acid then stirred an additional 1 hour and 45 minutes. The solvent was removed under reduced pressure, and the residue was taken up into 125 mL ethyl acetate. This was washed with 50 mL 10% sodium bicarbonate, dried ($MgSO_4$) and evaporated to give an oil, which was purified by flash chromatography over silica gel, eluting with ethyl acetate to give 150 mg of trans-5,6,7,7a,8,12b-hexahydro-2-methoxy-3-chloro-7-methyl-benz[d]indeno[2,1-b]azepine (Compound Q) as an oil, 200 MHz NMR ($CDCl_3$) d 2.17(dd,1H,J=12,Hz), 2.69(m,2H) 2.37(s,3H), 2.90–3.40(m,4H), 3.77(s,3H), 4.67(d,1H,J=9 Hz), 7.03(s,1H), 7.17(s,1H), 7.20–7.35(m,4H).

G.

trans-5,6,7,7a,8,12b-Hexahydro-2-hydroxy-3-chloro-7-methyl-benz[d]indeno[2,1-b]azepine hydrobromide A solution of 147 mg (0.47 mmol) of Compound Q from Step F above in 10 mL methylene chloride at −78° C. was treated with 90 mL boron tribromide, and the mixture was stirred for 4 hours while coming to room temperature. The reaction was quenched with 10 mL dry methanol and stirred for 10 minutes. The solvent was evaporated under reduced pressure, and the residue was treated with a second 10 mL portion of methanol. After 10 minutes, the solvent was evaporated at 10 mm Hg and 50° C. for 45 minutes to give 180 mg (100%) of the crude hydrobromide, 200 MHz NMR(d6-DMSO) d 2.97(s,3H), 2.90–3.90(m,7H),5.02(d,1H,J=8 Hz),6.99(s,1H),7.36(m,5H).

By application of the above-described techniques and related procedures known to those skilled in the art, the compounds listed in Table II below may also be synthesized.

TABLE II

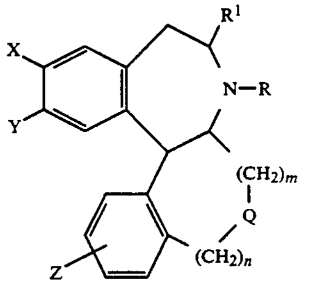

| Q | n | m | X | Y | Z | $R^1$ | R |
|---|---|---|---|---|---|---|---|
| $CH_2$ | 0 | 0 | $OCH_3$ | OH | H | H | $CH_3$ |
| $CH_2$ | 1 | 1 | Cl | OH | H | H | $CH_3$ |
| $CH_2$ | 1 | 1 | $OCH_3$ | OH | H | H | $CH_3$ |
| $CH_2$ | 1 | 1 | H | OH | H | H | $CH_3$ |
| S | 0 | 1 | Cl | OH | H | H | $CH_3$ |
| S | 0 | 1 | $OCH_3$ | OH | H | H | $CH_3$ |
| S | 0 | 1 | $CH_3$ | OH | H | H | $CH_3$ |
| S | 0 | 1 | H | OH | H | H | $CH_3$ |
| O | 0 | 1 | Cl | OH | H | H | $CH_3$ |
| O | 0 | 1 | $OCH_3$ | OH | H | H | $CH_3$ |
| O | 0 | 1 | H | OH | H | H | $CH_3$ |
| O | 0 | 1 | $CH_3$ | OH | H | H | $CH_3$ |
| $CH_2$ | 1 | 0 | Cl | OH | H | H | $CH_3$ |
| $CH_2$ | 1 | 0 | $OCH_3$ | OH | H | H | $CH_3$ |
| $CH_2$ | 1 | 0 | Cl | OH | H | H | H |
| $CH_2$ | 1 | 0 | H | $NH_2$ | H | H | $CH_3$ |
| $CH_2$ | 1 | 0 | $CH_3$ | $NH_2$ | H | H | $CH_3$ |
| $CH_2$ | 1 | 0 | Cl | $NH_2$ | H | H | $CH_3$ |
| $CH_2$ | 1 | 0 | H | OH | H | H | $CH_3$ |
| $CH_2$ | 1 | 0 | $CH_3$ | OH | H | H | $CH_3$ |
| $CH_2$ | 1 | 0 | Cl | * | H | H | $CH_3$ |

TABLE II-continued

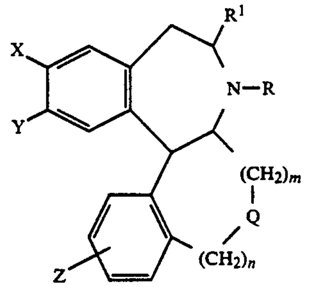

| Q | n | m | X | Y | Z | $R^1$ | R |
|---|---|---|---|---|---|---|---|
| $CH_2$ | 1 | 0 | $CH_3O$ | * | H | H | $CH_3$ |
| $CH_2$ | 1 | 0 | $CH_3O$ | OH | H | $CH_3$ | $CH_3$ |
| $CH_2$ | 1 | 0 | H | OH | 11-Cl | H | $CH_3$ |
| $CH_2$ | 0 | 0 | Cl | OH | H | H | H |

Note: * = $-OCON(CH_3)_2$

The following formulations illustrate depot formulations of the invention and may employ any of the compounds of the invention, e.g., (−)-trans-6,7,7a,8,9,13b-hexahydro-3-chloro-2-hydroxy-7-methyl-5H-benzo[d-]naphtho[2,1-b]azepine:

EXAMPLE 16

| DEPOT FORMULATIONS | mg/g | mg/g |
|---|---|---|
| Active Ingredient | 300 | 300 |
| Avicel RC 591 | 20 | — |
| Benzalkonium Chloride | 0.15 | — |
| Edetate Disodium | 0.1 | — |
| Methylparaben | — | 1.8 |
| Propylparaben | — | 0.2 |
| Peanut Oil to make | — | 1 g |
| Water for Injection to make | 1 g | — |

While the present invention has been described in conjunction with the specific embodiments set forth above, many alternatives, modifications and variations thereof will be apparent to those of ordinary skill in the art. All such alternatives, modifications and variations are intended to fall within the spirit and scope of the present invention.

We claim:

1. A compound of formula XIV

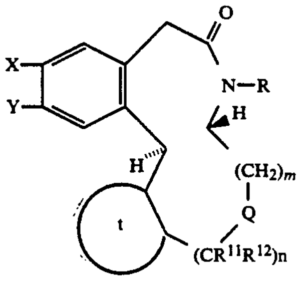

XIV or a pharmaceutically acceptable salt or isomer thereof, wherein

R is hydrogen, alkyl, —CH2CH=CH2 or

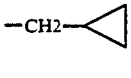

Q is methylene;

m is 1; n is zero;

X is hydrogen, halo, alkyl, alkylthio, alkylsulfinyl, alkylsulfonyl, hydroxy, alkoxy or trifluoromethyl;

Y is hydrogen, hydroxy, alkoxy,

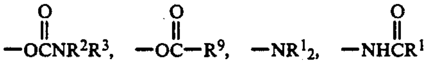

or

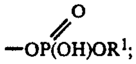

$R^1$, $R^{11}$ and $R^{12}$ are the same or different and each is hydrogen or alkyl;

ring

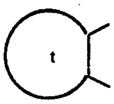

represents a fused benzene ring, said fused benzene ring optionally being substituted with a substituent Z as defined below;

$R^2$ and $R^3$ are independently hydrogen (provided that both are not hydrogen), alkyl, aralkyl, cycloalkyl, aryl, hydroxyalkyl, or alkoxyalkyl;

in still further addition, when $R^2$ is hydrogen, $R^3$ may additionally be $-CHR^7CO_2R^8$, wherein $R^7$ and $R^8$ are independently hydrogen, alkyl or aralkyl;

$R^9$ is alkyl, aralkyl, aryl, alkoxyalkyl, aryloxyalkyl, aralkoxyalkyl, cycloalkylalkyl, alkoxycarbonylalkyl, cycoalkyl, 1-adamantyl, cycloalkoxyalkyl, alkoxy, aralkoxy, cycloalkoxy, aryloxy or $-CHR^7NHR^8$ wherein $R^7$ and $R^8$ are as defined above; and Z is X as defined above, amino alkylamino and

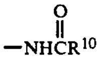

wherein $R^{10}$ is hydrogen, alkyl or aryl.

2. A compound according to claim 1 wherein Y is

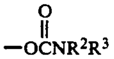

wherein $R^2$ and $R^3$ are both alkyl or one of $R^2$ and $R^3$ is hydrogen and the other is alkyl, $-NHR^1$ wherein $R^1$ is hydrogen or methyl,

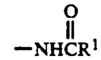

wherein $R^1$ is hydrogen or methyl,

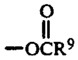

wherein $R^9$ is as defined in claim 1, or hydroxy.

3. A compound according to claim 1 wherein Y is $-OH$ or $-NH_2$.

4. A compound according to claim 3 wherein X is hydrogen, alkyl, halo or alkoxy.

5. A compound according to claim 4 wherein ring

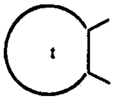

represents a fused benzene ring and Z is hydrogen, halo, alkyl, hydroxy or alkoxy.

6. A compound according to claim 5 wherein R is methyl.

7. A compound according to claim 1 having the structural formula

Ia

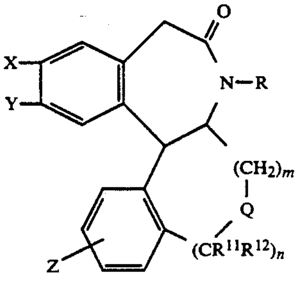

Ia wherein R, Q, X, Y, Z, m and n are as defined in claim 1 and $R^{11}$ and $R^{12}$ are both H.

8. A compound according to claim 7, wherein:

R is methyl;

Q is methylene;

the sum of m+n equals 1;

X is hydrogen, methyl, methoxy, chloro or bromo;

Y is hydroxy, amino,

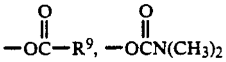

or $-NHCH_3$ wherein $R^9$ is as defined in claim 1; and

Z is hydrogen, halo, alkyl or $-OR^1$ wherein $R^1$ is as defined in claim 1; or pharmaceutically acceptable salts thereof.

9. A compound having the structure

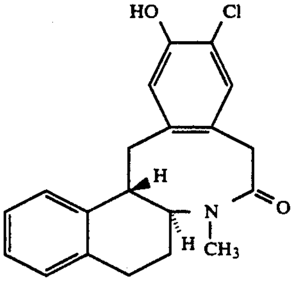

* * * * *

UNITED STATES PATENT AND TRADEMARK OFFICE
CERTIFICATE OF CORRECTION

PATENT NO. : 5,302,716

DATED : April 12, 1994

INVENTOR(S) : Joel G. Berger, et al.

It is certified that error appears in the above-identified patent and that said Letters Patent is hereby corrected as shown below:

Claim 1, Column 36, Lines 50-60, Formula XIV should appear as follows:

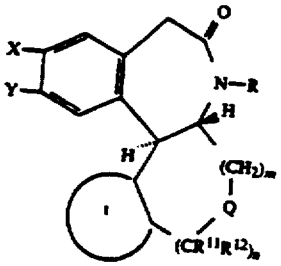

Signed and Sealed this

Eleventh Day of October, 1994

*Attest:*

BRUCE LEHMAN

*Attesting Officer*

*Commissioner of Patents and Trademarks*